(12) United States Patent
Wada

(10) Patent No.: US 7,909,460 B1
(45) Date of Patent: Mar. 22, 2011

(54) APPARATUS FOR MEASURING DOWNWARD ROTATION AMOUNT OF EYEBALL AND METHOD FOR MEASURING DOWNWARD ROTATION AMOUNT OF EYEBALL

(75) Inventor: Osamu Wada, Ina (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 12/877,847

(22) Filed: Sep. 8, 2010

(30) Foreign Application Priority Data

Oct. 1, 2009 (JP) ................................. 2009-229408

(51) Int. Cl.
*A61B 3/10* (2006.01)

(52) U.S. Cl. ....................................................... 351/204

(58) Field of Classification Search .................. 351/204, 351/246, 205, 200, 177, 178; 382/282; 33/507, 33/200
See application file for complete search history.

(56) References Cited

U.S. PATENT DOCUMENTS

| | | | | |
|---|---|---|---|---|
| 6,533,418 B1 * | 3/2003 | Izumitani et al. | ............. | 351/204 |
| 6,659,609 B2 * | 12/2003 | Mothes | .......................... | 351/204 |
| 6,827,443 B2 | 12/2004 | Fisher et al. | .................. | 351/209 |
| 7,441,895 B2 | 10/2008 | Akiyama et al. | .............. | 251/206 |
| 2010/0195045 A1 * | 8/2010 | Nauche et al. | ................ | 351/204 |

FOREIGN PATENT DOCUMENTS

| | | |
|---|---|---|
| JP | 2003-523244 | 8/2003 |
| JP | 2005-342186 | 12/2005 |
| JP | 2008-521027 | 6/2008 |
| WO | WO 2005/092173 A1 | 10/2005 |
| WO | WO 2006/054985 A1 | 5/2006 |

\* cited by examiner

*Primary Examiner* — Hung X Dang
(74) *Attorney, Agent, or Firm* — DLA Piper LLP (US)

(57) ABSTRACT

An apparatus for measuring a downward rotation amount of eyeball that measures a length from a distance-vision eye point to a near-vision eye point of a spectacle lens actually worn by a wearer and attached to a frame having an upper side portion and a lower side portion, includes: a line-of-sight position detecting unit that detects a position of a line of sight corresponding to the distance-vision eye point of the wearer and a position of a line of sight corresponding to the near-vision eye point; and a computing unit that computes a distance between the position of the distance-vision eye point and the position of the near-vision eye point detected by the line-of-sight position detecting unit, wherein the line-of-sight position detecting unit has an arm member that is rotatable at one end and positioned at a lateral position of an eyeball of the wearer, a front detecting mechanism that is disposed on the other end side of the arm member and detects a front position of the eyeball of the wearer, and an arm rotation angle detecting unit that detects a rotation angle of the arm member.

7 Claims, 21 Drawing Sheets

FIG.13

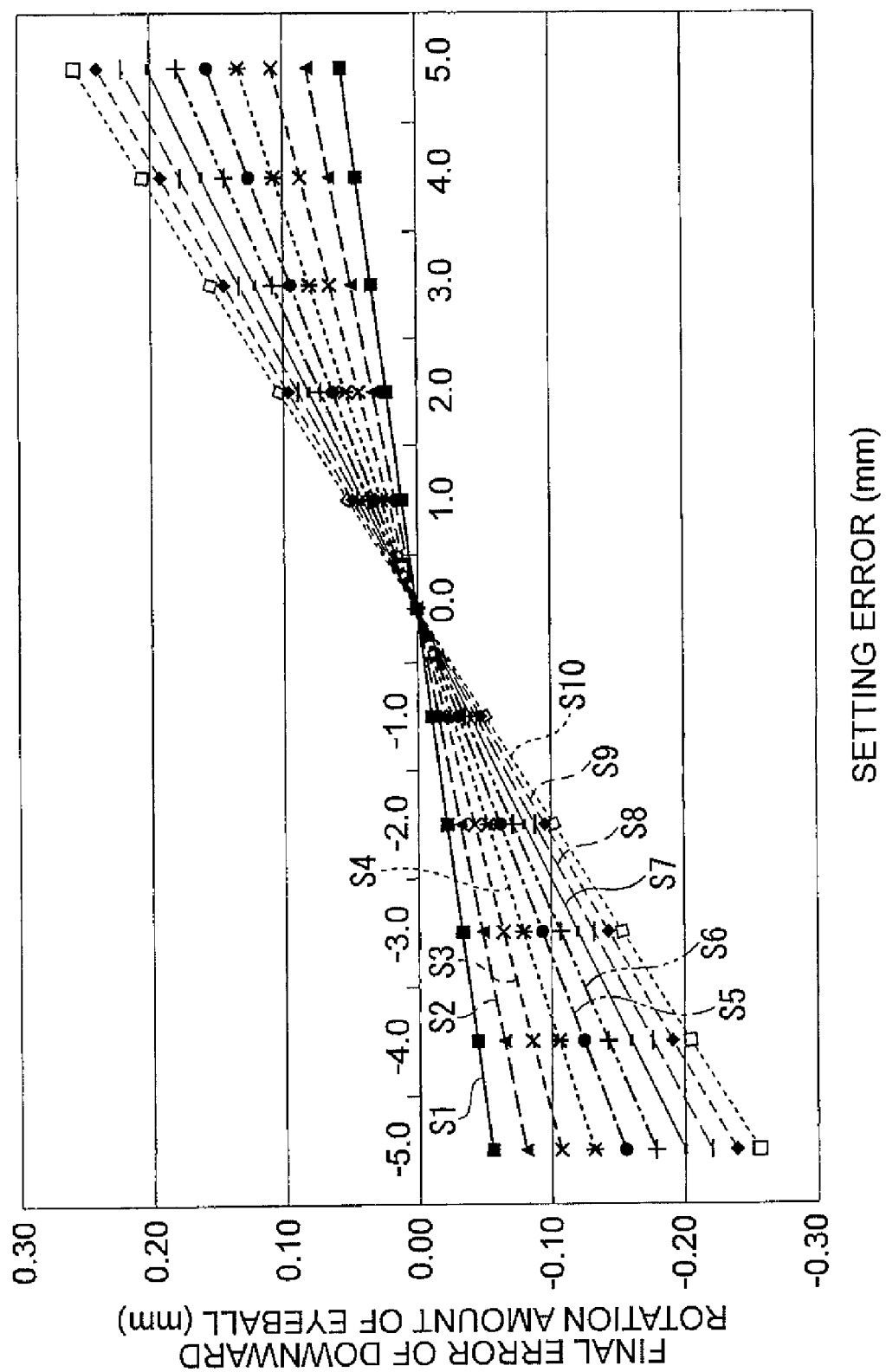

APPARATUS FOR MEASURING DOWNWARD ROTATION AMOUNT OF EYEBALL AND METHOD FOR MEASURING DOWNWARD ROTATION AMOUNT OF EYEBALL

BACKGROUND

1. Technical Field

The present invention relates to an apparatus for measuring a downward rotation amount of eyeball and a method for measuring a downward rotation amount of eyeball in a spectacle lens.

2. Related Art

Spectacle lenses include progressive power spectacle lenses in addition to single-vision spectacle lenses. The progressive power lens is an aspherical lens including a distance portion area having a refractive power (diopter) corresponding to distance vision and a near portion area having a refractive power corresponding to near vision. The distance portion area is set at an upper position of the lens, the near portion area is set at a lower position of the lens, and a progressive zone in which the refractive power progressively changes is provided between the areas. There is no border separating these areas, and a user can look at objects from far to near with one lens. The distance portion area, the near portion area, and the progressive zone need adjustments according to an individual's intended use (far and near focusing, intermediate and near focusing, near and near focusing, full-time use, part-time use, static use, dynamic use, etc.) (optical fittings). Among the optical fittings, a downward rotation amount of eyeball is important for the progressive power lens. The "downward rotation amount of eyeball" is, when a line-of-sight position on the lens in a state where a spectacles wearer views at eye level is defined as a distance-vision eye point (FP), and a line-of-sight position on the lens in a state of a line of sight for near vision is defined as a near-vision eye point (NP), a distance of the downward rotation of an eyeball from the distance-vision eye point to the near-vision eye point.

For designing such a spectacle lens, there is a related art in which, by analyzing an individual's eye movement path in a state of wearing spectacles using software with information from an eye movement measuring apparatus, one or more eye points or an average area is specified, and, based on the information, a spectacle lens is custom-designed by modifying a standard lens according to the individual's eye (JP-T-2008-521027). In the related art of JP-T-2008-521027, the eye movement measuring apparatus is used for measuring an eye point.

Moreover, there is a related art (JP-T-2003-523244) in which a head tracking system and values derived from the result of statistical analysis of a wearer behavioral statistical model are used, the wearer's individual visual behavioral patterns are determined, and a most suitable lens design is recommended with guidance on the choice of frame from a plurality of known lenses.

In the related art of JP-T-2008-521027, since the eye movement measuring apparatus is used, the apparatus is expensive as a whole. Since not only a head and an eye movement but also the posture of a person who wears spectacles (wearer) is involved in determining the distance-vision eye point or the near-vision eye point, the related art of JP-T-2008-521027 in which the points are determined only with the head and the eye movement cannot obtain a correct measured value.

In the related art of JP-T-2003-523244, similarly to the JP-T-2008-521027, since the head tracking system is used, not only is the apparatus expensive as a whole, but also the measurement cannot be accurately performed depending on the wearer's posture.

SUMMARY

An advantage of some aspects of the invention is to provide an apparatus for measuring a downward rotation amount of eyeball that can accurately and inexpensively determine a downward rotation amount of eyeball according to an individual wearer and a method for measuring a downward rotation amount of eyeball.

A first aspect of the invention is directed to an apparatus for measuring a downward rotation amount of eyeball that measures a length from a distance-vision eye point to a near-vision eye point of a spectacle lens actually worn by a wearer and attached to a frame having an upper side portion and a lower side portion, including: a line-of-sight position detecting unit that detects a position of a line of sight corresponding to the distance-vision eye point of the wearer and a position of a line of sight corresponding to the near-vision eye point; and a computing unit that computes a distance between the position of the distance-vision eye point and the position of the near-vision eye point detected by the line-of-sight position detecting unit, wherein the line-of-sight position detecting unit has an arm member that is rotatable at one end and positioned at a lateral position of an eyeball of the wearer, a front detecting mechanism that is disposed on the other end side of the arm member and detects a front position of the eyeball of the wearer, and an arm rotation angle detecting unit that detects a rotation angle of the arm member.

In the first aspect of the invention with this configuration, the near-vision eye point and the distance-vision eye point that are different in line-of-sight position of an eye are detected by the line-of-sight position detecting unit in a state of wearing spectacles. For detecting the points, the rotatable one end of the arm member is first positioned so as to be positioned at the lateral side of the eyeball of the wearer; thereafter, for example, the wearer is caused to face forward; the inclination angle of the arm member in that state is detected by the arm rotation angle detecting unit; the wearer is further caused to lower his/her line of sight; the arm member is inclined so that the pupil of the wearer is positioned at the front in that state, which is detected by the front detecting mechanism; and the inclination angle of the arm member at this position is detected by the arm rotation angle detecting unit. Based on the downward rotation angle of eyeball of the arm member, the downward rotation amount of eyeball that is the distance between the position of the distance-vision eye point and the position of the near-vision eye point is computed by the computing unit.

In the first aspect of invention, therefore, since the distance-vision eye point and the near-vision eye point are detected in a natural posture regardless of the wearer's posture, the downward rotation amount of eyeball can be measured accurately and simply. Moreover, since the expensive eye Movement measuring apparatus and the expensive software that analyzes the eye movement path based on the information output from the apparatus, as in the related art, are not required, the apparatus can be provided inexpensively. Especially since the line-of-sight position detecting unit is configured to include the arm member, the front detecting mechanism, and the arm rotation angle detecting unit, the position of the pupil of the wearer is not detected based on an image but based on the inclination angle of the arm member for determining the distance-vision eye point and the near-vision eye point. Therefore, the structure of the line-of-sight position detecting unit is more simplified, which can ensure a cost reduction in the apparatus.

In the first aspect of the invention, it is preferable that the arm member is rotatably supported to an arm supporting member at the one end side, and the arm supporting member is rotatably attached to a supporting column.

In the first aspect of the invention with this configuration, by adjusting the rotation angle of the arm member with respect to the arm supporting member and by further adjusting the rotation angle of the arm supporting member with respect to the supporting column, the positioning of the rotatable one end of the arm member to the wearer can be easily performed. Therefore, the measurement of the downward rotation amount of eyeball can be performed with good accuracy.

It is preferable that the arm supporting member can expand and contract.

In the first aspect of the invention with this configuration, by expanding or contracting the arm supporting member, the positioning of the one end of the arm member to the wearer can be easily performed. Therefore, the measurement of the downward rotation amount of eyeball can be performed with good accuracy.

It is preferable that the apparatus further includes wearer chairs each arranged on opposite sides of the supporting column, and that the arm supporting member is rotatable at its distal end side so as to be positioned on opposite sides of the supporting column.

In the first aspect of the invention with this configuration, the wearer sits on one of the wearer chairs arranged at two locations; the downward rotation amount of eyeball in one eyeball (right eye) of the wearer is measured by the above-described procedures; thereafter, the wearer sits anew on the other wearer chair; the arm supporting member is rotated with respect to the supporting column by 180 degrees; and in this state, the downward rotation amount of eyeball in one eyeball (left eye) of the wearer is measured by the above-described procedures.

Accordingly, in the first aspect of the invention, even when the downward rotation amount of eyeball is different between the right and left eyeballs, the different downward rotation amounts of the right and left eyeballs can be accurately measured.

It is preferable that the front detecting mechanism is a camera.

In the first aspect of the invention with this configuration, the image of the front position of the wearer can be accurately and reliably picked up using the camera. Also in view of this, therefore, the measurement accuracy can be improved, and in addition, the cost of the apparatus can be reduced.

A second aspect of the invention is directed to a method for measuring a downward rotation amount of eyeball using the apparatus for measuring the downward rotation amount of eyeball having the above-described configuration, including: causing the wearer to face forward in a state of wearing the spectacle lens and determining a position of the spectacle lens corresponding to the pupil of the wearer as a distance-vision eye point line; positioning the rotatable one end of the arm member at the lateral position of the eyeball of the wearer; detecting, by the front detecting mechanism, that the pupil of the wearer is positioned on the distance-vision eye point line at the front and detecting, by the arm rotation angle detecting unit, an inclination angle of the arm member at this front position as a first angle; detecting, by the front detecting mechanism, that the pupil of the wearer is positioned at the near-vision eye point at the front in a state where the wearer lowers his/her line of sight and detecting, by the arm rotation angle detecting unit, an inclination angle of the arm member at this position as a second angle; and calculating, by the computing unit, a distance between the position of the distance-vision eye point and the position of the near-vision eye point based on a downward rotation angle of eyeball determined from a difference between the inclination angle detected in the detecting the first angle and the inclination angle detected in the detecting the second angle.

A third aspect of the invention is directed to a method for measuring a downward rotation amount of eyeball using the apparatus for measuring the downward rotation amount of eyeball having the above-described configuration, including: causing the wearer to face forward in a state of wearing the spectacle lens and determining a position of the spectacle lens corresponding to the pupil of the wearer as a distance-vision eye point line; positioning the rotatable one end of the arm member at the lateral position of the eyeball of the wearer; detecting, by the front detecting mechanism, that the pupil of the wearer is positioned at the near-vision eye point at the front in a state where the wearer lowers his/her line of sight and detecting, by the arm rotation angle detecting unit, an inclination angle of the arm member at this position as a first angle; detecting, by the front detecting mechanism, that the pupil of the wearer is positioned on the distance-vision eye point line at the front in a state where the wearer raises his/her line of sight and detecting, by the arm rotation angle detecting unit, an inclination angle of the arm member at this front position as a second angle; and calculating, by the computing unit, a distance between the position of the distance-vision eye point and the position of the near-vision eye point based on a downward rotation angle of eyeball determined from a difference between the inclination angle detected in the detecting the first angle and the inclination angle detected in the detecting the second angle.

According to these methods for measuring the downward rotation amount of eyeball, the downward rotation amount of eyeball can be determined easily and accurately using the above-described apparatus for measuring the downward rotation amount of eyeball.

BRIEF DESCRIPTION OF THE DRAWINGS

The invention will be described with reference to the accompanying drawings, wherein like numbers reference like elements.

FIG. 13 is a schematic view of a table showing results computed by a computing section.

FIG. 21 is a graph showing a relation between the setting error of an arm member and the error of the downward rotation amount of eyeball.

DESCRIPTION OF EXEMPLARY EMBODIMENTS

Hereinafter, an embodiment of the invention will be described based on the drawings.

Figure 1:
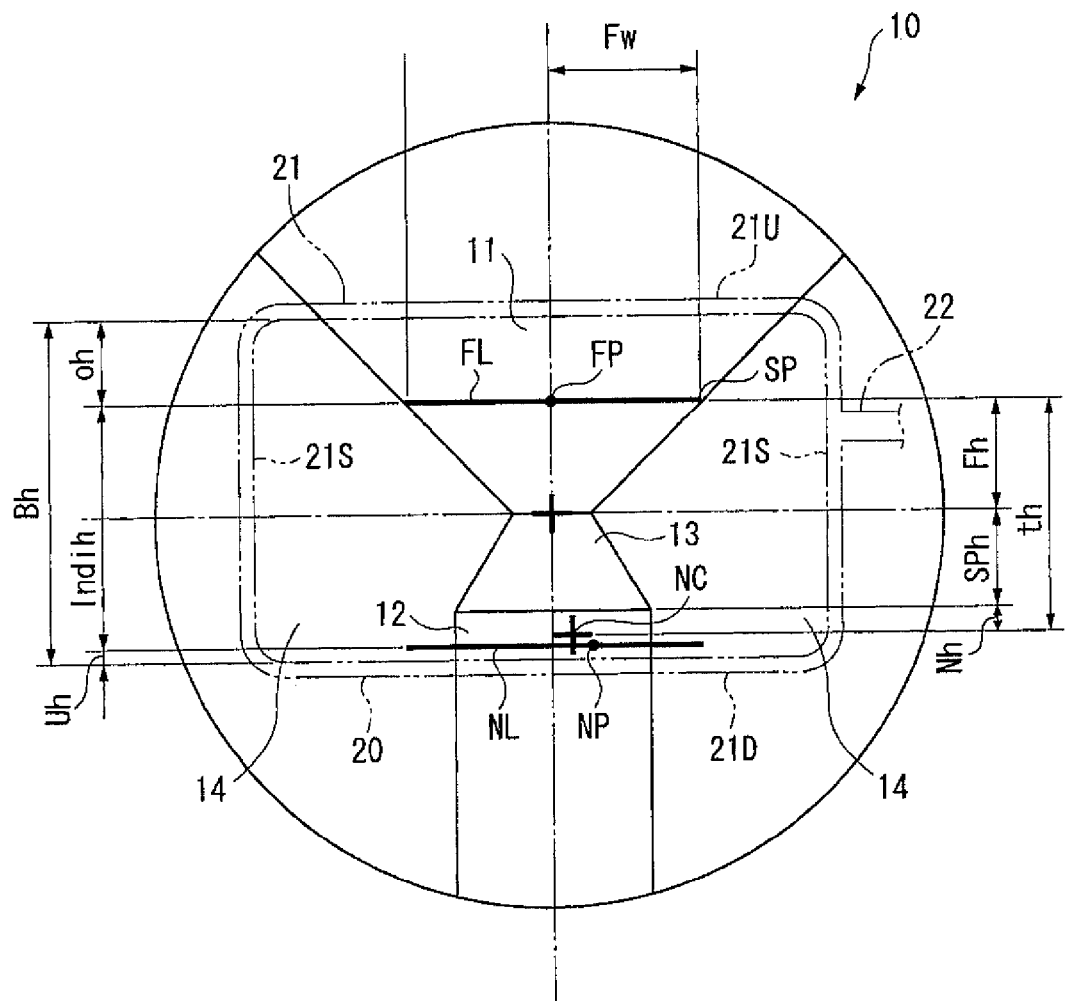
FIG. 1 is a schematic view of a spectacle lens measured by an apparatus for measuring a downward rotation amount of eyeball according to one embodiment of the invention.

In the embodiment, a progressive power lens is used as a spectacle lens. In the embodiment, the description will be made with a vertical direction when spectacles are being worn as an up-and-down direction and a horizontal direction when spectacles are being worn as a right-and-left direction.
Spectacle Lens As shown in FIG. 1, a spectacle lens 10 has a distance portion area 11 positioned at an upper portion of the lens, a near portion area 12 positioned at a lower portion thereof, a progressive zone 13 positioned between the distance portion area 11 and the near portion area 12, and side areas 14 adjacent to sides of the progressive zone 13.

The distance portion area 11 has a mean power with relatively low positive power that is suitable for distance vision. Especially a position through which a horizontal line passing through the center of a pupil (that is, a line of sight) passes when a wearer looks forward is defined as a distance-vision eye point FP. The distance-vision eye point FP is positioned at a point of intersection of a line extending from a geometric center of the spectacle lens upward in the vertical direction and a distance-vision eye point line FL.

The near portion area 12 has a mean power with relatively high positive power that is suitable for near vision (for example, reading books). Especially a position through which a line of sight passes when the wearer looks near (looks downward) is defined as a near-vision eye point NP.

The progressive zone 13 is an area where the relative, positive mean addition power changes progressively between the distance portion area 11 and the near portion area 12. The straight line passing through the distance-vision eye point FP and extending in the right-and-left direction is defined as the distance-vision eye point line FL. A distance from the distance-vision eye point FP to a boundary line between the distance portion area 11 and the side area 14 on the distance-vision eye point line FL is defined as a horizontal field-of-fixation width Fw.

A straight line passing through the near-vision eye point NP and extending in the right-and-left direction is defined as a near-vision eye point line NL. A distance (length) between the distance-vision eye point line FL and the near-vision eye point line NL is a downward rotation amount Indih of eyeball.

A distance-vision eye point height Fh is from a boundary line between the distance portion area 11 and the progressive zone 13 to the distance-vision eye point FP. A length (distance) from the boundary line between the distance portion area 11 and the progressive zone 13 to a boundary line between the progressive zone 13 and the near portion area 12 is a progressive zone length SPh.

A length (distance) from the boundary line between the progressive zone 13 and the near portion area 12 to an optical center NC of the near portion area 12 is a near portion height Nh. The optical center NC of the near portion area 12 is an optical center for the optical design of the near portion area.

The length (distance) between the optical center NC of the near portion area 12 and the boundary line between the near portion area 12 and the progressive zone 13 is the near portion height Nh.

The side area 14 is an area called an astigmatic area. Since the wearer sees double through the side area 14, the wearer generally does not look at an object through the side area 14.

The spectacle lens 10 is obtained by fabricating such a progressive power lens, and the obtained spectacle lenses 10 are attached to a frame 20 to serve as spectacles.

The frame 20 includes frame rims 21 each having the spectacle lens 10 attached thereto and surrounding the same in a frame shape, a bridge 22 coupling the right and left frame rims 21 together, and temples 23 (refer to FIG. 7) each rotatably attached from the frame rim 21 via a hinge. The frame rim 21 has an upper side portion 21U, a lower side portion 21D, and lateral side portions 21S. A distance between the upper side portion 21U and the lower side portion 21D is an edged lens height Bh of the spectacle lens. A distance from the distance-vision eye point FP to the upper side portion of the frame is an upper frame height Oh. A distance from the lower side portion 21D of the frame rim 21 to the near-vision eye point NP is a lower frame height Uh.

Figure 2:
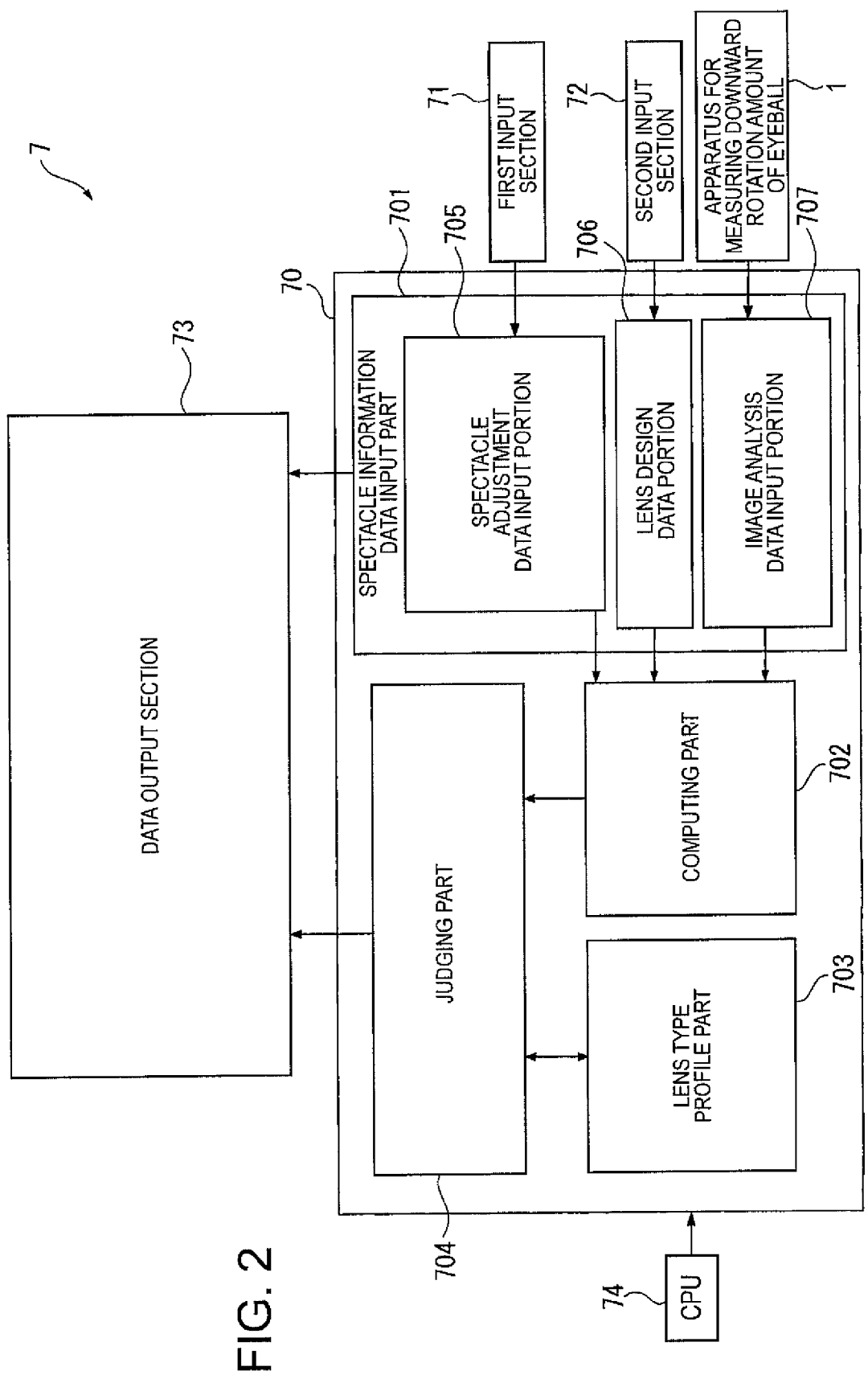
FIG. 2 is a block diagram showing the overall configuration of a spectacle lens selection system according to the embodiment.

FIG. 2 is a block diagram showing the overall configuration of a spectacle lens selection system of the embodiment.

In FIG. 2, the spectacle lens selection system includes an apparatus 1 for measuring a downward rotation amount of eyeball and a selection apparatus 7 that selects one spectacle lens from a plurality of types of spectacle lenses based on data sent from the apparatus 1 for measuring the downward rotation amount of eyeball. The selection apparatus 7 is configured to include a selection control section 70, a first input section 71, a second input section 72, a data output section 73, and a CPU 74 that controls the selection control section 70.

The first input section 71, which is composed of a keyboard, a pen, or the like, is an input unit for directly inputting to the selection apparatus 7.

The second input section 72 is a unit to which necessary information is input from lens manufacturers via communication means such as the Internet or a telephone line.

The apparatus 1 for measuring the downward rotation amount of eyeball measures the downward rotation amount Indih of eyeball that is the length from the distance-vision eye point FP to the near-vision eye point NP. As one example in the embodiment, the configuration of the apparatus 1 for measuring the downward rotation amount of eyeball is shown in FIGS. 3 to 6.

Figure 3:
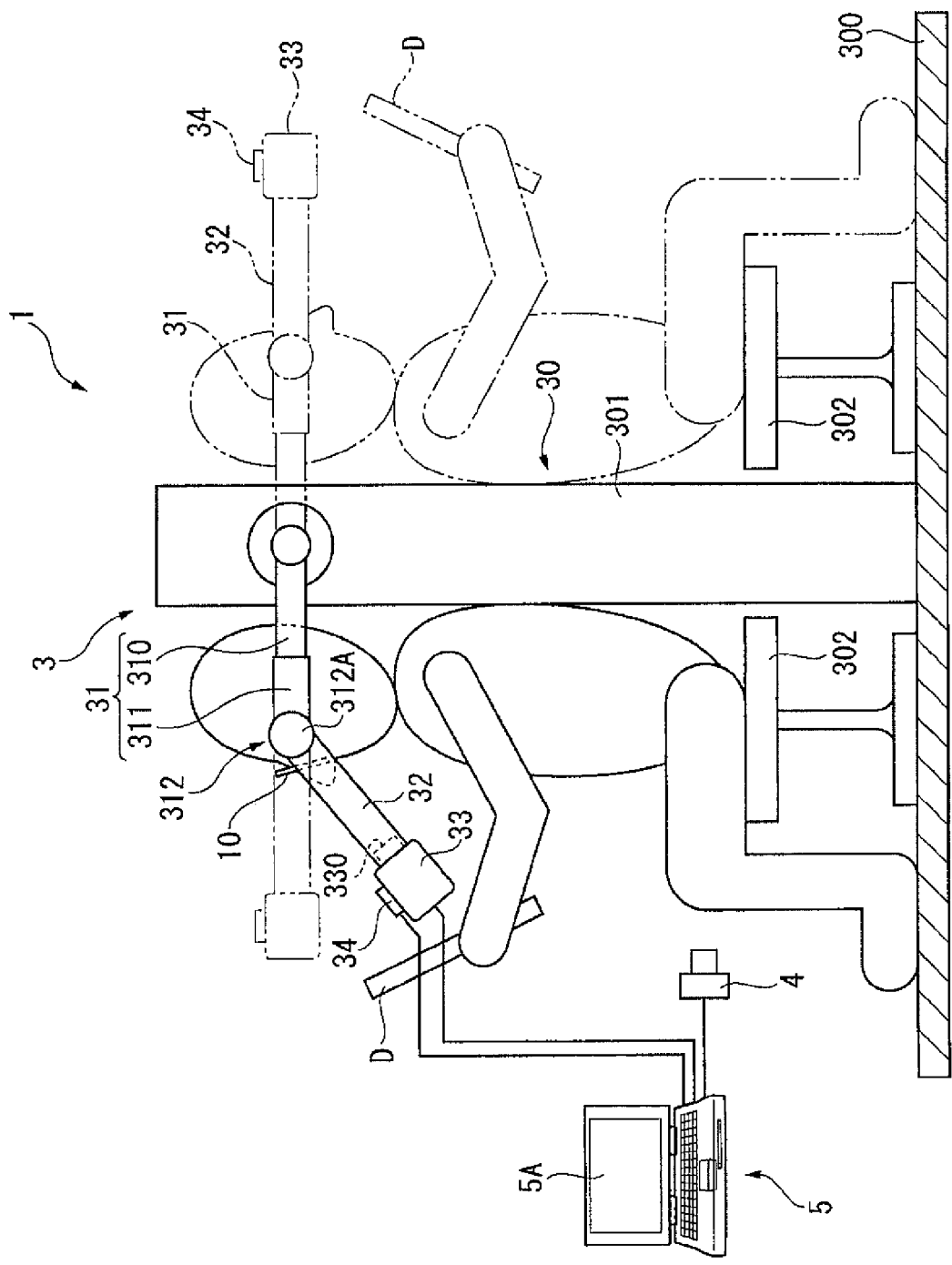
FIG. 3 is a schematic configuration view of the apparatus for measuring the downward rotation amount of eyeball according to the embodiment.

FIG. 3 is a schematic configuration view of the apparatus 1 for measuring the downward rotation amount of eyeball.

In FIG. 3, the apparatus 1 for measuring the downward rotation amount of eyeball includes a line-of-sight position detecting unit 3 that detects a wearer's line-of-sight position, a side image pickup unit 4 that measures a forward tilt angle θ of the frame provided with the spectacle lens 10, and a computing unit 5 that is composed of a personal computer and computes the downward rotation amount Indih of eyeball based on outputs from the line-of-sight position detecting unit 3 and the side image pickup unit 4.

The line-of-sight position detecting unit 3 detects a position of a line of sight corresponding to the distance-vision eye point FP of a wearer and a position of a line of sight corresponding to the near-vision eye point NP. The line-of-sight position detecting unit 3 includes a base stand 30, a rod-like arm supporting member 31 that is disposed for the base stand 30, an arm member 32 whose base end is rotatably disposed for the arm supporting member 31, a camera 33 that is disposed at a distal end of the arm member 32 as a front detecting mechanism, and an arm rotation angle detecting unit 34 that is disposed for the camera 33 and detects a rotation angle of the arm member 32.

The base stand 30 includes a base 300, a supporting column 301 that is disposed on the base 300, and wearer chairs 302 that are each arranged on opposite sides of the supporting column 301.

The arm supporting member 31 is rotatably attached to an upper side of the supporting column 301. The arm supporting member 31 is freely rotatable from a predetermined position, for example, a position that is orthogonal to the supporting column 301 and where the distal end is directed to the left in FIG. 3 as a starting point to a position that is directed to the right on the opposite side of the supporting column 301 in a vertical plane. That is, the arm supporting member 31 is rotatable at the distal end side so as to be positioned on opposite sides of the supporting column 301.

In the embodiment, the specific attachment structure of the arm supporting member 31 is not limited as long as it is freely rotatably attached to the supporting column 301. For example, the arm supporting member 31 may have a hinge structure in which it is disposed at the central position of the supporting column 301 in a right-and-left width direction. For automatically operating the rotation of the arm supporting member 31, the supporting column 301 is provided with a rotation mechanism (not shown) formed of a drive source such as a motor, a gear, and the like. In the embodiment, however, the rotation mechanism may be omitted, and the arm supporting member 31 may be rotationally operated manually. The arm supporting member 31 can be fixed with respect to the supporting column 301 at any angle.

Figure 4:
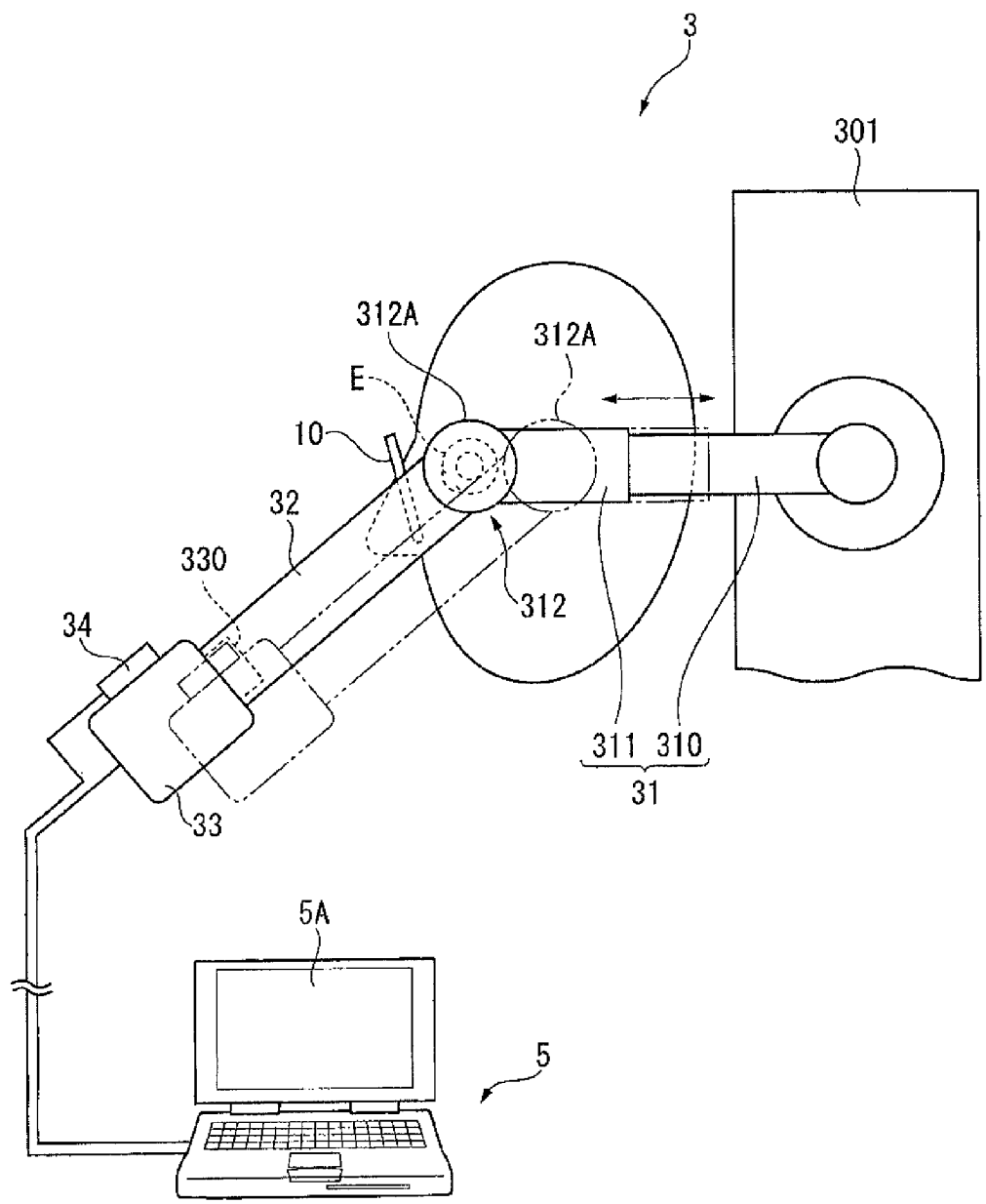
FIG. 4 is a schematic view showing the main part of the apparatus for measuring the downward rotation amount of eyeball.

FIG. 4 shows the configuration of the arm supporting member 31. In FIG. 4, the arm supporting member 31 includes a rectangular column portion 310 whose base end portion is freely rotatably supported by the supporting column 301 and a rectangular tube portion 311 in which the rectangular column portion 310 is freely telescopically housed. The arm supporting member 31 is freely telescopically configured in its axial direction.

The arm supporting member 31 further includes a fixing member (not shown) that fixes the rectangular tube portion 311 with respect to the rectangular column portion 310 at any position. The fixing member can employ an appropriate structure. For example, the fixing member may be a bolt that is screwed to a side surface portion of the rectangular tube portion 311 and whose tip end portion can be pressed to the circumferential surface of the rectangular column portion 310.

A rotation mechanism 312 for freely rotatably supporting the arm member 32 to the arm supporting member 31 in the vertical plane is disposed at the distal end portion of the rectangular tube portion 311 and the base end portion of the arm member 32. The rotation mechanism 312 horizontally extends in its axial direction and includes a shaft-like rotation portion 312A that couples the arm member 32 with the rectangular tube portion 311 and a drive mechanism (not shown) that causes the arm member 32 to rotate about the rotation portion 312A with respect to the rectangular tube portion 311. The drive mechanism is composed of a motor, a gear, and the like. The rotation portion 312A causes the arm supporting member 31 to expand and contract or rotate with respect to the supporting column 301, so that the arm supporting member 31 can be positioned at a lateral position of an eyeball of the wearer sat on the wearer chair 302. The rotation mechanism 312 of the embodiment does not require a specific configuration as long as it has a structure that can rotate the arm member 32 by any angle with respect to the rectangular tube portion 311 and can fix the same at the position. For example, the drive mechanism may be omitted.

Figure 5A:
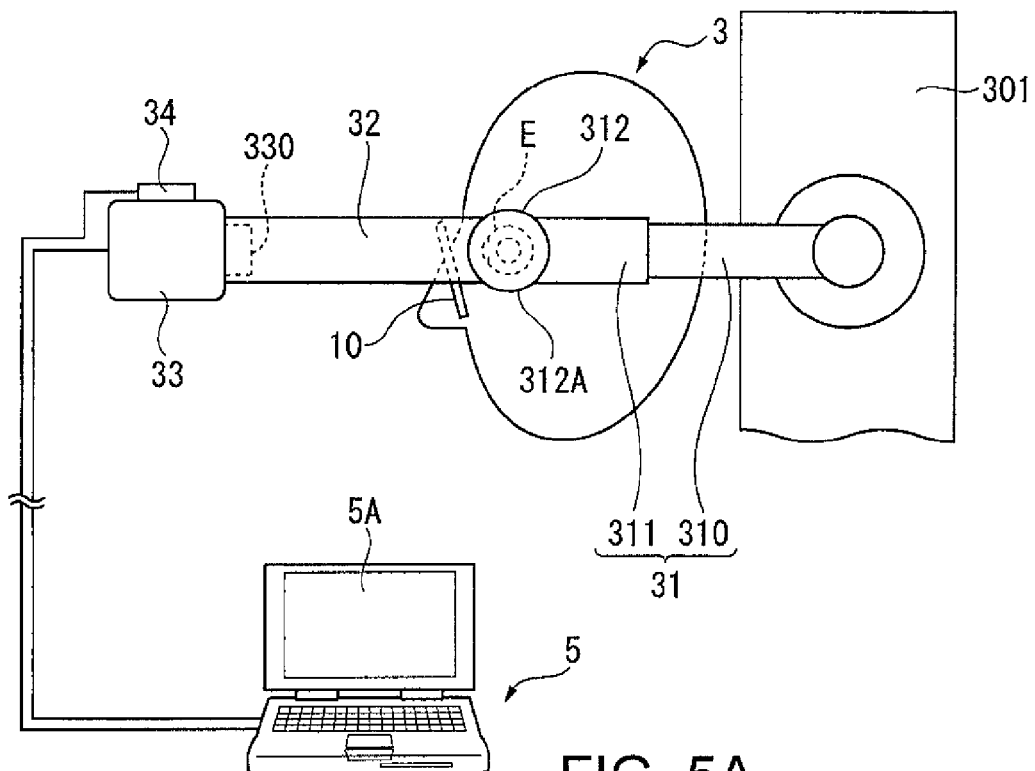
FIG. 5A is a schematic view for determining a distance-vision eye point.
Figure 5B:
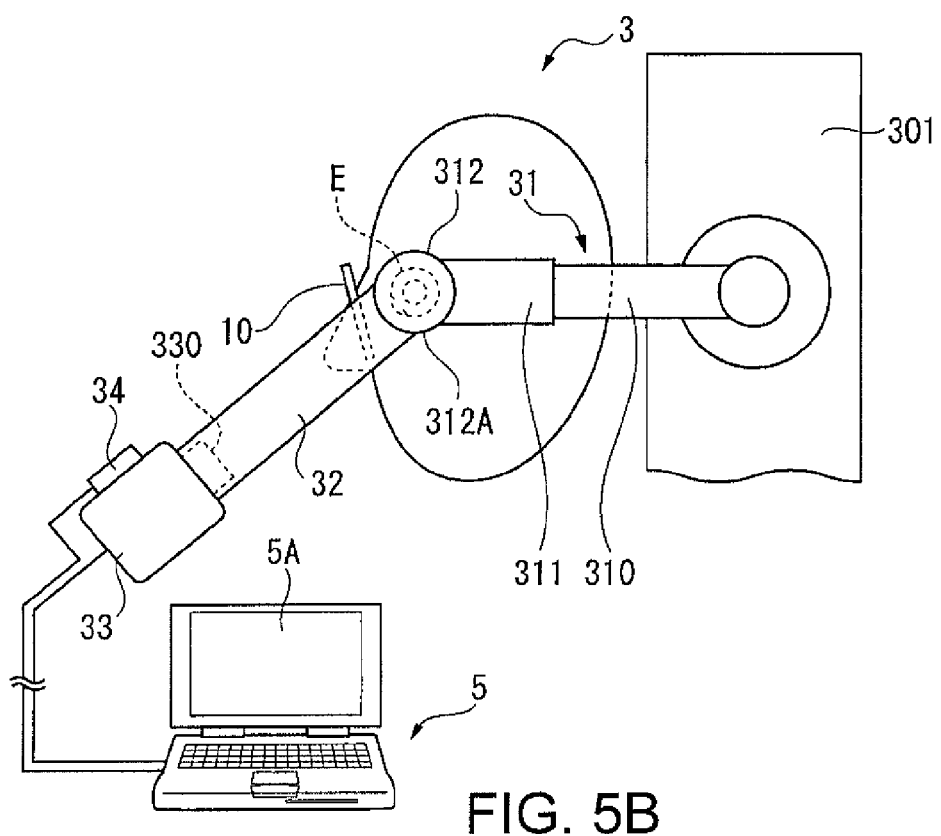
FIG. 5B is a schematic view for determining a near-vision eye point.

The camera 33 has at the distal end of the arm member 32 a lens 330 that is arranged so as to be directed to the rotation portion 312A. The image pickup signal of the camera 33 is output to the computing unit 5 as a digital signal. The camera picks up a front image focusing on an eye on one side of the wearer sat on the wearer chair 302 in a rotation range of the arm member 32. As shown in FIG. 5A for example, for obtaining the position of the distance-vision eye point, the lens 330 is directed to the horizontal direction to pick up a front image of the wearer focusing on his/her left eye. As shown in FIG. 5B, for obtaining the position of the near-vision eye point, the lens 330 is directed obliquely upward from the lower position to pick up a front image of the wearer focusing on the left eye. In FIGS. 5A and 5B, the position of the distance-vision eye point or the near-vision eye point is obtained when a pupil portion is located at the front.

The arm rotation angle detecting unit 34 is a digital goniometer whose main body of a detecting portion that detects the inclination angle of the arm member 32 is housed in a casing. The casing is fixed to an upper portion of the camera 33 with a magnet or other means.

In the arm rotation angle detecting unit 34, any inclination angle can be set to zero. A detected signal detected by the arm rotation angle detecting unit 34 is output to the computing unit 5.

Figure 6A:
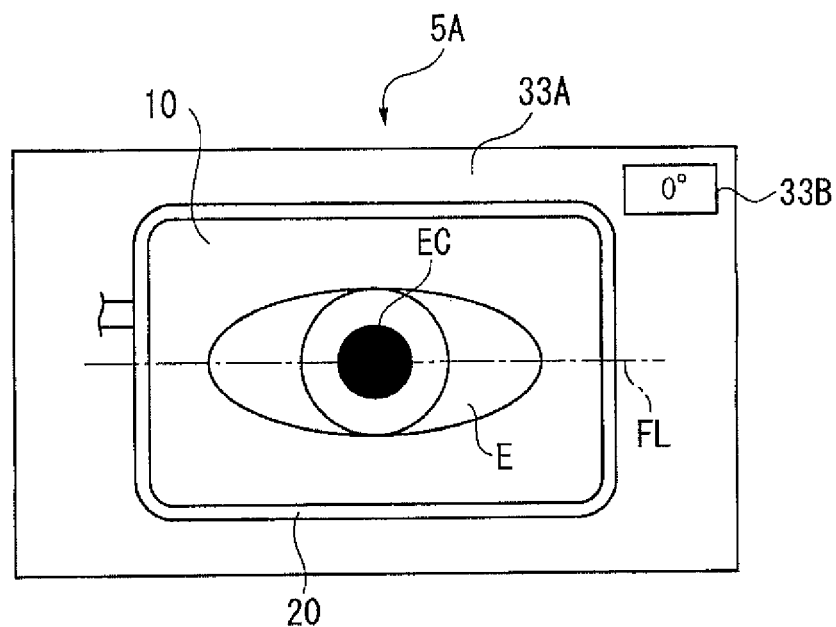
FIGS. 6A and 6B are each a schematic view of an image of a wearer wearing spectacles picked up by a camera.
Figure 6B:
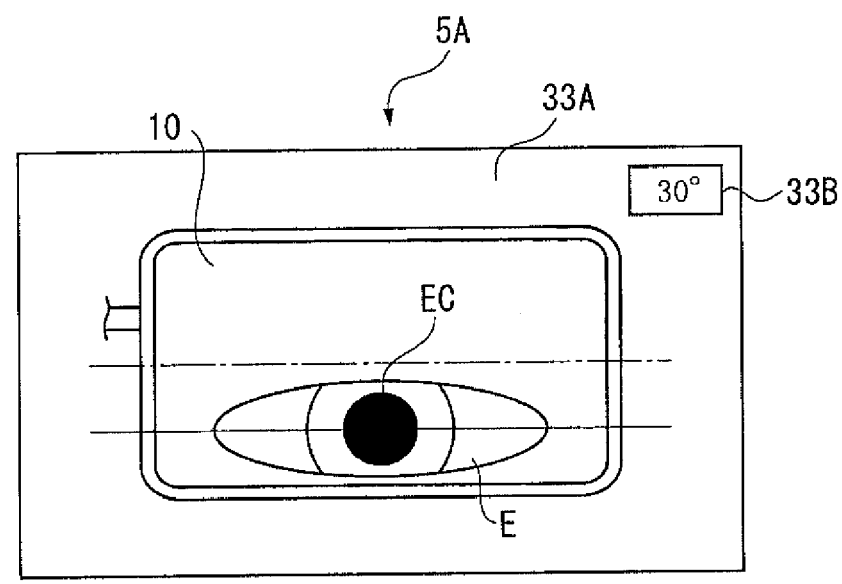

An image 33A picked up by the camera 33 and an inclination, angle display part 33B for displaying the inclination angle detected by the arm rotation angle detecting unit 34 are displayed on a display section 5A of the computing unit 5 (refer to FIGS. 6A and 6B). That is, the display section 5A displays the image 33A of the front of the wearer wearing the spectacle lens 10 according to the inclination angle of the arm member 32 and displays the inclination angle of the arm member 32 at that time in the inclination angle display part 33B.

Returning to FIG. 3, the side image pickup unit 4 functions as a forward tilt angle measuring unit and includes a camera that picks up a side image of the wearer wearing the spectacles provided with the spectacle lenses 10 and an image processing section that determines a forward tilt angle θ of the frame 20 based on the image picked up by the camera.

Figure 7:
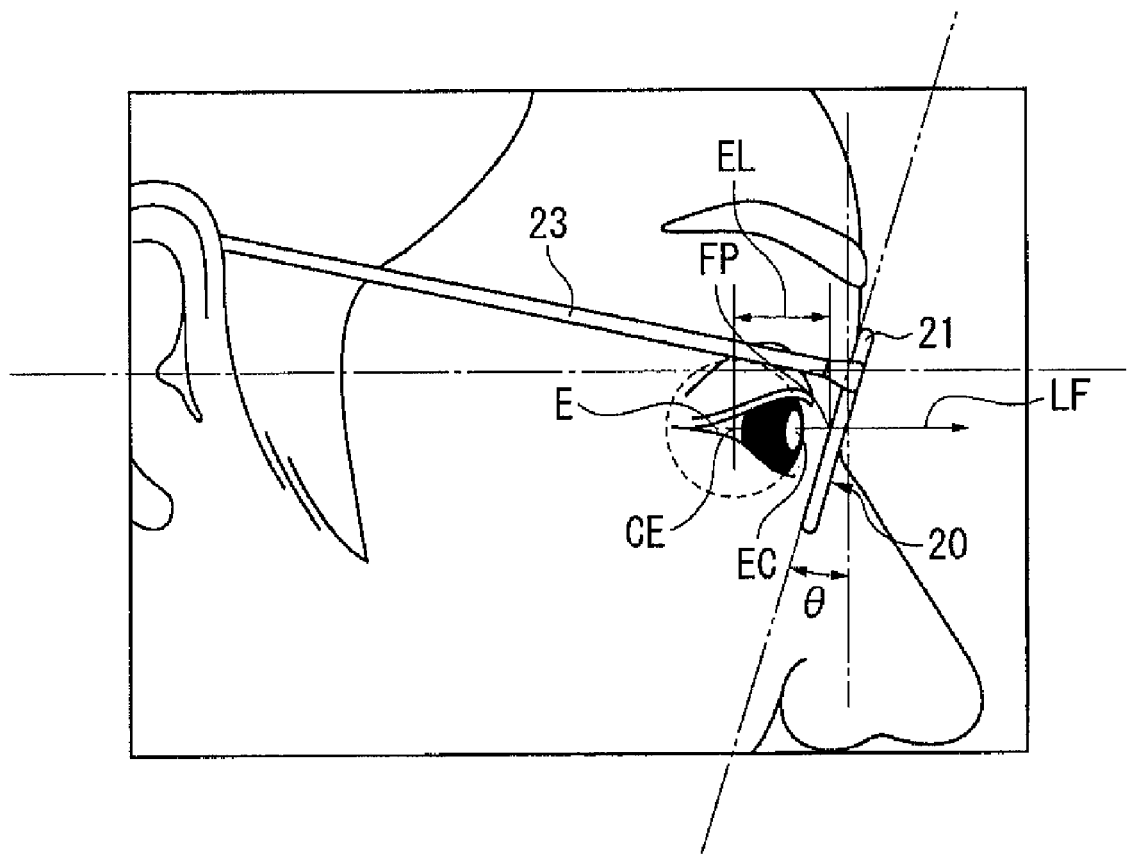
FIG. 7 is a schematic view of an image picked up by a side image pickup unit.

FIG. 7 shows an image picked up by the side image pickup unit 4.

In FIG. 7, the image is picked up in a state where the wearer faces in the horizontal direction. Based on the image of the position of the temple 23, the position of the frame rim 21, and the like of the frame 20 of the wearer, the image processing section calculates the forward tilt angle θ. Data of the forward tilt angle θ calculated by the image processing section is sent to the computing unit 5.

In the embodiment, the image processing section may be omitted, and a worker may directly determine the forward tilt angle θ based on the screen picked up by the camera and separately input the numerical value to the computing unit 5.

In FIG. 3, the computing unit 5 is a personal computer including an external input section such as a keyboard, the display section 5A, and a computing section, and computes the downward rotation amount Indih of eyeball based on information output from the camera 33 and the side image pickup unit 4 and other information.

The downward rotation amount Indih of eyeball is the distance (length) between the distance-vision eye point line FL and the near-vision eye point line NL. In the embodiment, the downward rotation amount Indih of eyeball is computed in units of 0.5 mm.

Figure 8:
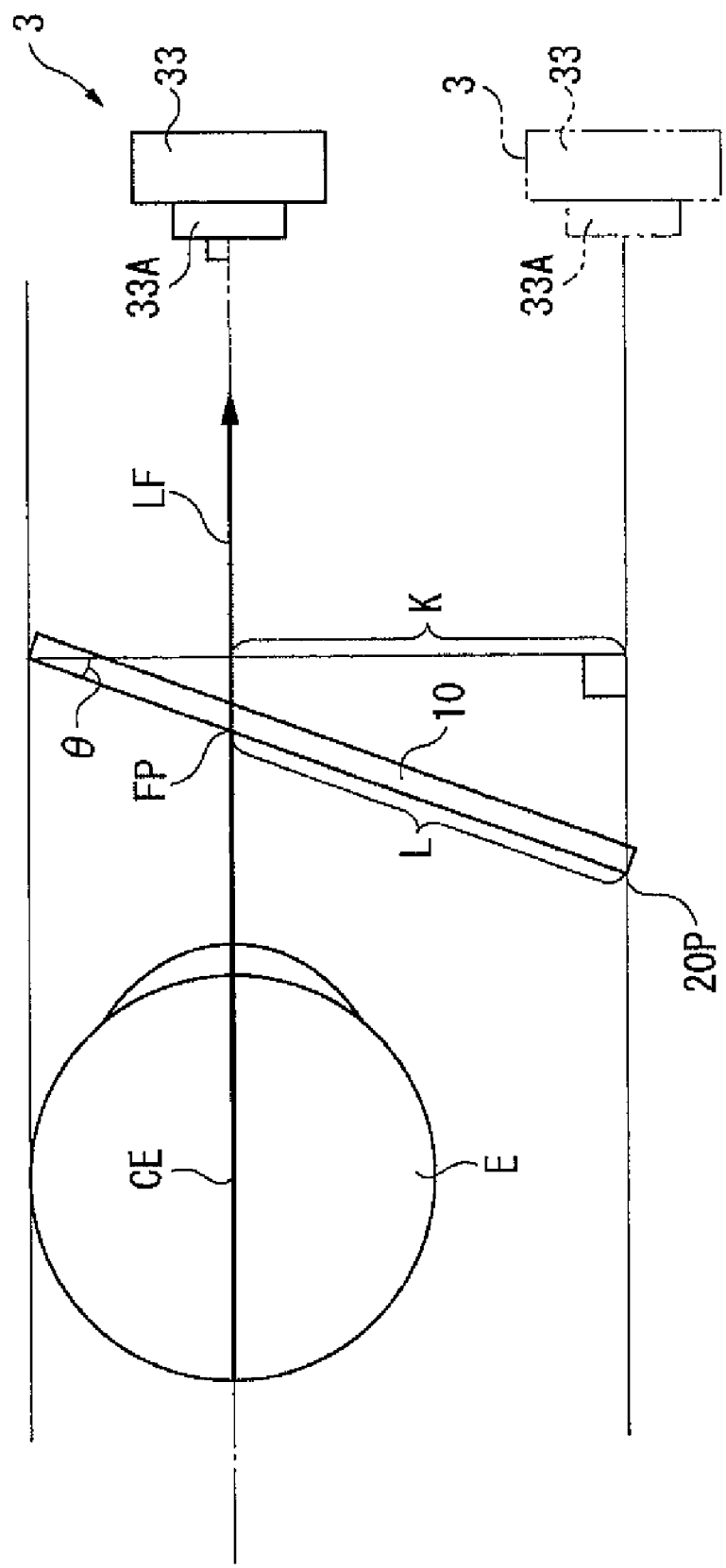
FIG. 8 is a schematic view for explaining the determination of a length of the distance-vision eye point.
Figure 9:
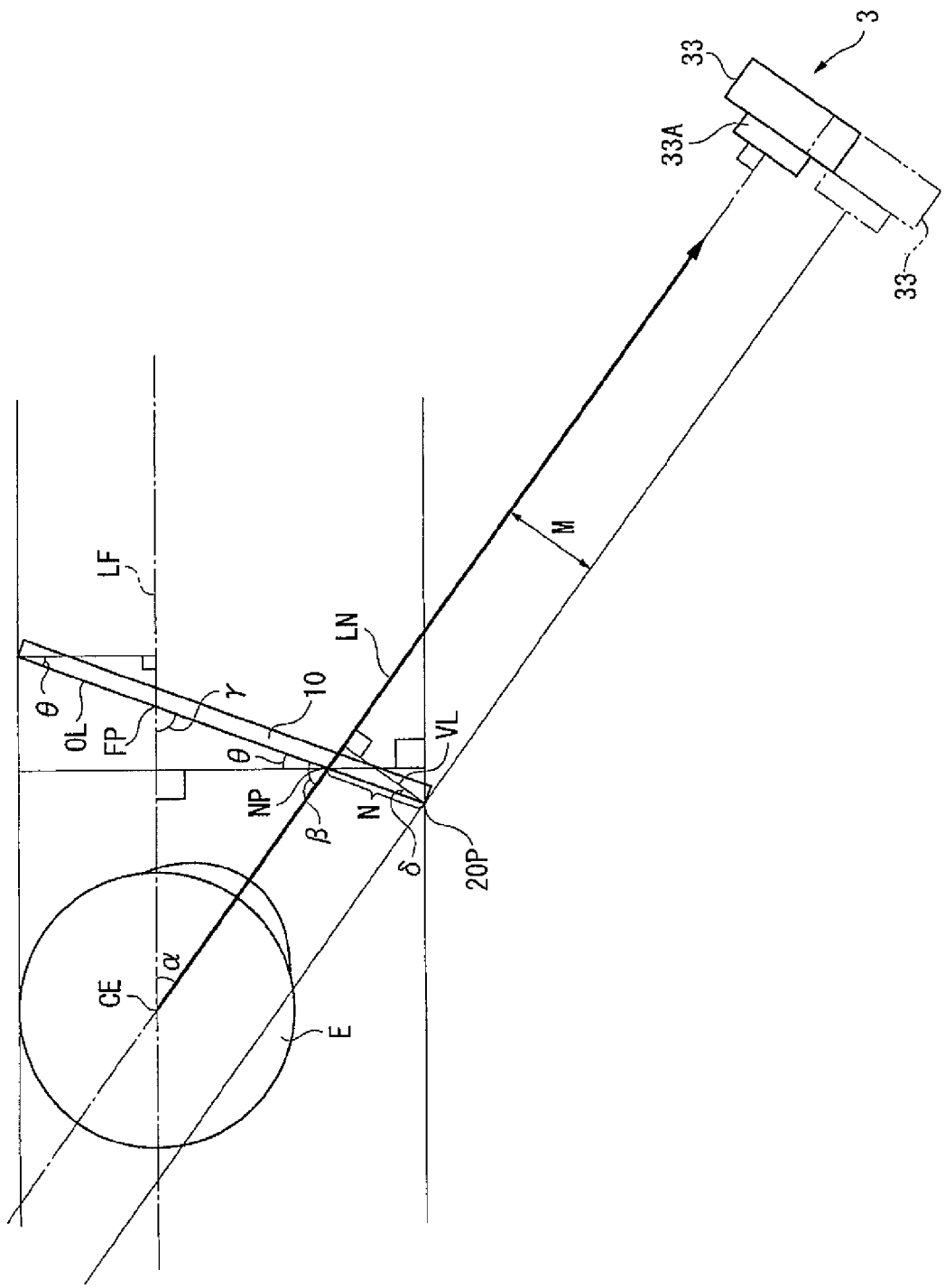
FIG. 9 is a schematic view for explaining the determination of a length of the near-vision eye point.

FIG. 8 shows a schematic view for explaining the determination of a length of the distance-vision eye point. FIG. 9 shows a schematic view for explaining the determination of a length of the near-vision eye point.

As shown in FIGS. 8 and 9, based on the forward tilt angle θ input from the side image pickup unit 4, a front line of sight LF connecting an eyeball center and the distance-vision eye point FP determined by the camera 33, a downward line of sight LN connecting the eyeball center and the near-vision eye point NP, a downward rotation angle α of eyeball that is the angle between the front line of sight LF and the downward line of sight LN, an angle β between the downward line of sight LN and an eyeball-side flat surface OL of the spectacle lens, an angle γ between the eyeball-side flat surface OL of the spectacle lens and the front line of sight LF, an angle δ between the eyeball-side flat surface OL of the spectacle lens and a normal line VL drawn from the position of a lower end 20 to the downward line of sight LN, a distance K between the position of the lower end 20P of the frame 20 on the spectacle side surface and the front line of sight LF, and a distance M of the normal line VL drawn from the position of the lower end 20P on the spectacle side surface to the downward line of sight LN, a length N of the near-vision eye point from the lower end 20P of the frame 20 to the near-vision eye point NP are determined by the following equations (a) to (d). The distance K is also an apparent length between the distance-vision eye point FP and the lower end 20P of the spectacle lens 10, while the distance M is an apparent length between the near-vision eye point NP and the lower end 20P of the spectacle lens 10.

$$N = M/\cos \delta \quad (a)$$

$$\delta = 180° - (\beta + 90°) \quad (b)$$

$$\beta = 180° - (\alpha + \gamma) \quad (C)$$

$$\gamma = 180° - (90° + \theta) \quad (d)$$

A length L of the distance-vision eye point from the lower end 20P of the frame 20 on the spectacle side surface to the distance-vision eye point FP is determined by the following equation (e).

$$L = K/\cos \theta \quad (5)$$

Further, since the downward rotation amount Indih of eyeball is the distance between the distance-vision eye point FP and the near-vision eye point NP, the downward rotation amount Indih of eyeball is determined by the following equation (f)

$$\text{Indih} = L - N \quad (f)$$

In the embodiment, the above equations are stored in a memory of the computing unit 5.

The distance K between the position of the lower end 20P of the frame 20 on the spectacle side surface and the front line of sight LF can be determined as a moving distance of the camera 33 when the camera is moved from a position at which it receives light with the front line of sight LF as the center to a position at which it receives light with the lower end 20P as the center. Similarly, the distance M between the position of the lower end 20P and the downward line of sight LN can be determined as a moving distance when the camera 33 is moved from a position at which it receives light with the downward line of sight LN as the center to a position at which it receives light with the lower end 20P as the center. Although the moving locus of the camera 33 is an arc, the moving locus can be approximated as a parallel shift because the moving distance is shorter compared to the distance between the eyeball and the camera 33.

Figure 10:
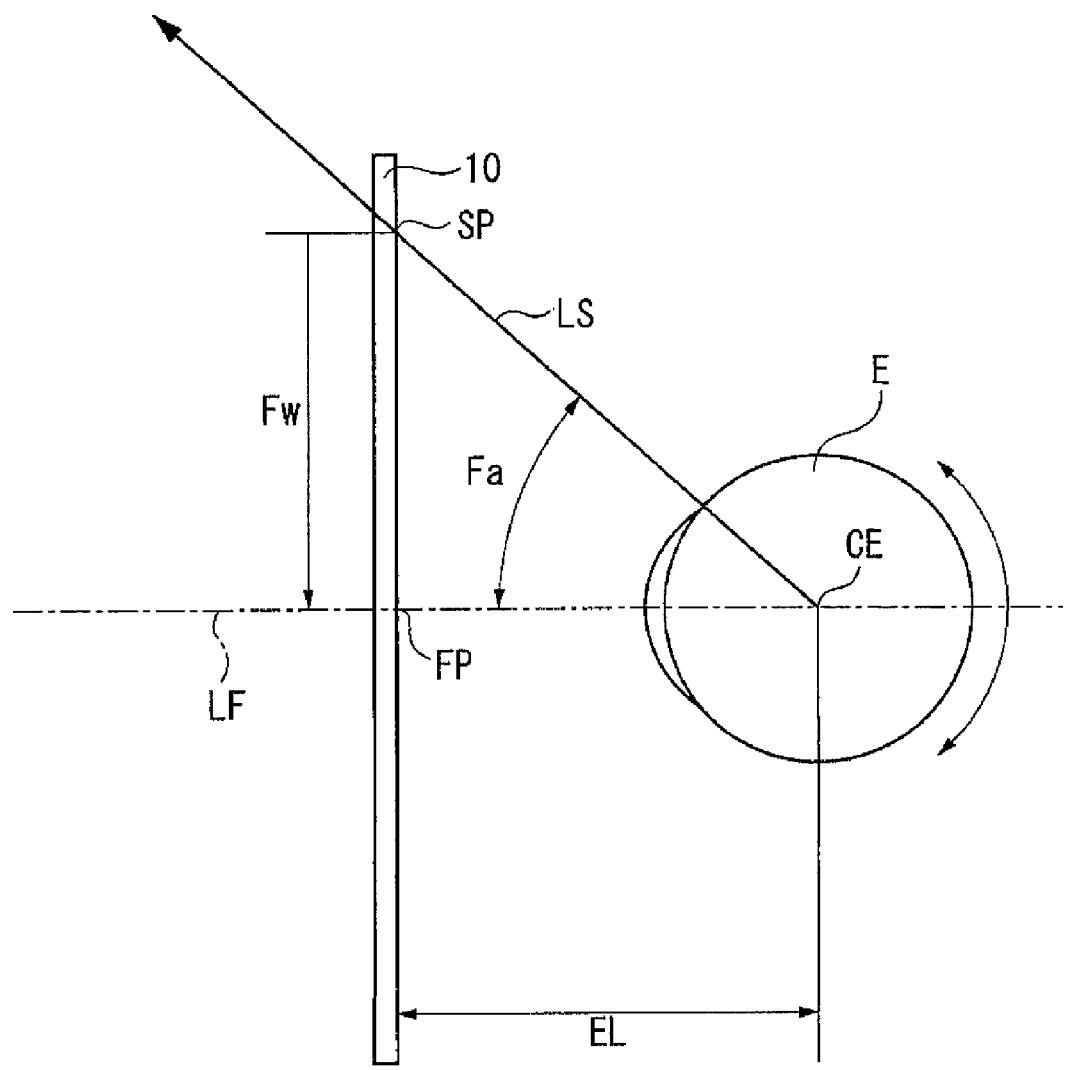
FIG. 10 is a schematic view showing a relation between a horizontal field-of-fixation angle and a spectacle wearing distance.

FIG. 10 is a schematic view showing the relation between a horizontal field-of-fixation angle and a spectacle wearing distance. In FIG. 10, a horizontal field-of-fixation width Fw is a line segment extending from the distance-vision eye point FP of the spectacle lens 10 that is actually worn and is a length of a range that the wearer can look without turning his/her head. That is, on the distance-vision eye point line FL of the spectacle lens 10 on the eyeball side surface, a distance from the distance-vision eye point FP positioned at the point of intersection of the line extending from the geometric center of the spectacle lens 10 upward in the vertical direction and the distance-vision eye point line FL to a position SP that the wearer can look when the line of sight is shifted laterally without turning his/her head portion is the horizontal field-of-fixation width Fw.

An angle between the front line of sight LF passing through the distance-vision eye point FP and a straight line LS connecting an eyeball center CE and the position SP is defined as a horizontal field-of-fixation angle Fa. When a distance between the distance-vision eye point FP and the eyeball center CE is defined as a spectacle wearing distance EL, the horizontal field-of-fixation width Fw can be determined by the following equation.

$$Fw = EL \tan Fa \quad (g)$$

The side image pickup unit 4 also functions as a horizontal field-of-fixation width determining device that determines the horizontal field-of-fixation width Fw.

The side image pickup unit 4 has the image processing section. The image processing section estimates the position of the eyeball center CE of the wearer from the size or the like of an eyeball E based on the image picked up by the camera, measures the spectacle wearing distance EL that is the distance between the eyeball center CE and the distance-vision eye point FP based on the image, and calculates the horizontal field-of-fixation width Fw from the spectacle wearing distance EL and the horizontal field-of-fixation angle Fa that is previously input thereto based on the equation (g). Data of the horizontal field-of-fixation width Fw calculated by the image processing section is sent to the computing unit 5. In the embodiment, the image processing section may be omitted, and a worker may directly determine the spectacle wearing distance EL based on the screen picked up by the camera and separately input the numerical value to the computing unit 5 to thereby calculate the horizontal field-of-fixation width Fw by the computing unit 5.

In the embodiment, the horizontal field-of-fixation angle Fa is a value determined with reference to existent data. Although there are slight variations between individuals, a range searched only with an eyeball is conceivably from 10° to 15° in the right and left horizontal direction, and the better viewing condition is created by turning the head portion for wider viewing field (refer to "Binocular function and spectacles" written by Toyohiko Hatada, "Megane no Kagaku", 1977, Vol. 1, pp. 35 to 37, edited by the Japanese Society of Opthalmological Optics).

Figure 11A:
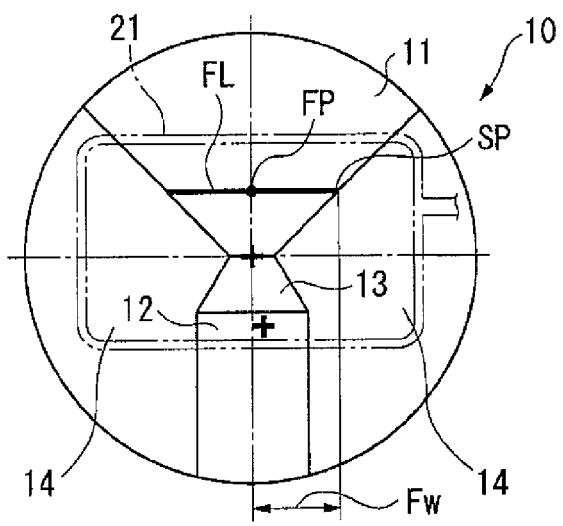
FIGS. 11A to 11C are schematic views showing three kinds of spectacle lenses different in length of the horizontal field-of-fixation width in a type with a narrow distance portion area.
Figure 11B:
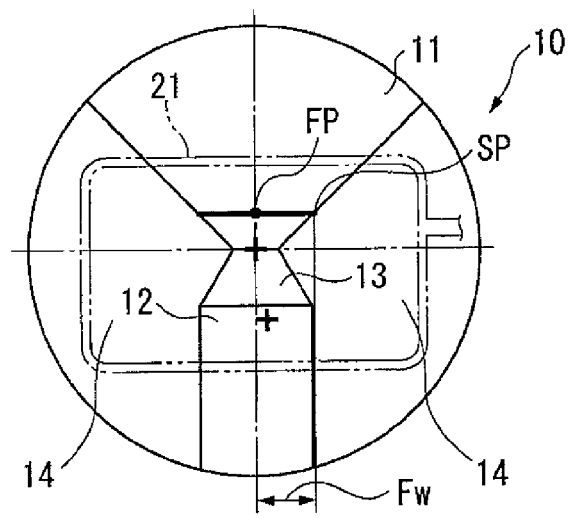
Figure 11C:
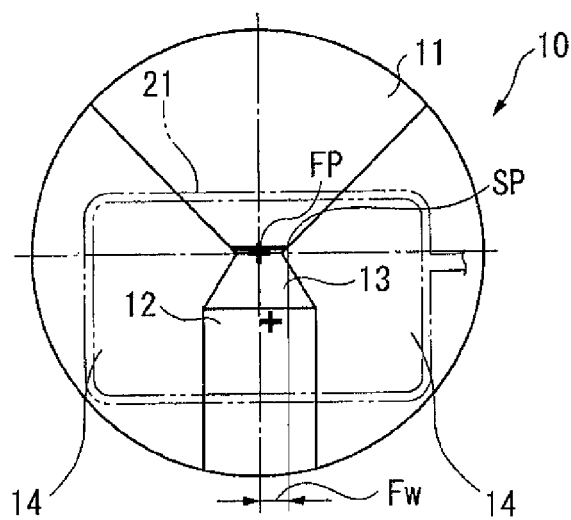

FIGS. 11A to 11C show three kinds of spectacle lenses 10 different in length of the horizontal field-of-fixation width Fw in a type having a narrow distance portion area 11.

FIG. 11A shows the horizontal field-of-fixation width Fw of a far- and near-focused spectacle lens 10. The far- and near-focused spectacle lens 10 is used for looking at both a distant scene and a nearby document. In the spectacle lens 10 shown in FIG. 11A for example, the horizontal field-of-fixation angle Fa is 13° or more, and the horizontal field-of-fixation width Fw is 6 mm or more.

FIG. 11B shows the horizontal field-of-fixation width Fw of an intermediate- and near-focused spectacle lens 10. The intermediate- and near-focused spectacle lens 10 is used for looking at both a medium-range scene and a nearby document. In the spectacle lens 10 shown in FIG. 11B for example, the horizontal field-of-fixation angle Fa has a value of greater than 0° and less than 13°, and the horizontal field-of-fixation width Fw is greater than 0 mm and less than 6 mm.

FIG. 11C shows the horizontal field-of-fixation width Fw of a near- and near-focused spectacle lens 10. The near- and near-focused spectacle lens 10 is used for looking at both a document on a desk and a document at hand both positioned nearby. In the spectacle lens 10 shown in FIG. 11C for example, the horizontal field-of-fixation width Fw is 0 mm or less.

As shown in FIGS. 11A to 11C, the far- and near-focused spectacle lens 10 shown in FIG. 11A has the longest horizontal field-of-fixation width Fw; the near- and near-focused spectacle lens 10 shown in FIG. 11C has the shortest horizontal field-of-fixation width Fw; and the intermediate- and near-focused spectacle lens shown in FIG. 113 has an intermediate length. In this manner, the horizontal field-of-fixation width Fw varies depending on the type of the spectacle lens 10. In the embodiment, the horizontal field-of-fixation angle Fa is, for example, Fw≧13° in the far- and near-focused spectacle lens 10, while being 0<Fw<13° in the intermediate- and near-focused, and near- and near-focused spectacle lenses 10. The far- and near-focused spectacle lens 10, the intermediate- and near-focused spectacle lens 10, and the near- and near-focused spectacle lens 10 have respectively constant values.

In FIG. 2, the selection control section 70 includes a spectacle information data input part 701, a computing part 702, a lens type profile part 703, and a judging part 704.

The spectacle information data input part 701 includes a spectacle adjustment data input portion 705, a lens design data portion 706, and an image analysis data input portion 707.

The spectacle adjustment data input portion 705 stores data such as data indicating how to use, optometry data, frame data, fitting data. These pieces of data are input from the first input section 71. The data stored in the spectacle adjustment data input portion 705 includes lens prescription data such as power of lens, addition power, spherical power, cylindrical power, cylindrical axis, and prismatic power, and also the distance-vision eye point height Fh, the near portion height Nh, the edged lens height Bh, and the progressive zone length SPh. These pieces of data of the distance-vision eye point height Fh, the near portion height Nh, the edged lens height Bh, and the progressive zone length SPh are input in units of 0.5 mm.

The lens design data portion 706 stores a prescription lens design profile. This data is input by the second input section 72. The prescription lens design profile is various data necessary for lens design and is information provided from lens manufacturers. The prescription lens design profile includes also the calculating equations used in the computing part 702.

The image analysis data input portion 707 stores data of the downward rotation amount Indih of eyeball and the spectacle wearing distance EL, front-viewing eye image analysis data, and downward viewing image analysis data. These pieces of data are sent from the apparatus 1 for measuring the downward rotation amount of eyeball.

The computing part 702 implements a later-described computation based on data sent from the spectacle adjustment data input portion 705, the lens design data portion 706, and the image analysis data input portion 707.

That is, the computing part 702 determines ΔE based on the downward rotation amount Indih of eyeball, the distance-vision eye point height Fh, the progressive zone length SPh, and the near portion height Nh by the equations (h) and (i), and determines ΔBh based on the ΔE, the edged lens height Bh of the spectacle lens, the upper frame height Oh, a total length th of the distance-vision eye point height Fh, the progressive zone length SPh, and the near portion height Nh, and the lower frame height Uh by the equation (j).

$$th = Fh + SPh + Nh \tag{h}$$

$$\Delta E = \text{Indih} - th \tag{i}$$

$$\Delta Bh = Bh - (Oh + th + \Delta E + Uh) \tag{j}$$

The lens type profile part 703 is input with basic information of three types, i.e., type A with a wide distance portion area 11, type B with an intermediate distance portion area 11, and type C with a narrow distance portion area 11 for each of the far- and near-focused spectacle lens 10, the intermediate- and near-focused spectacle lens 10, and the near- and near-focused spectacle lens 10. These pieces of information are input from the input unit such as the first input section 71 or the second input section 72.

Figure 12A:
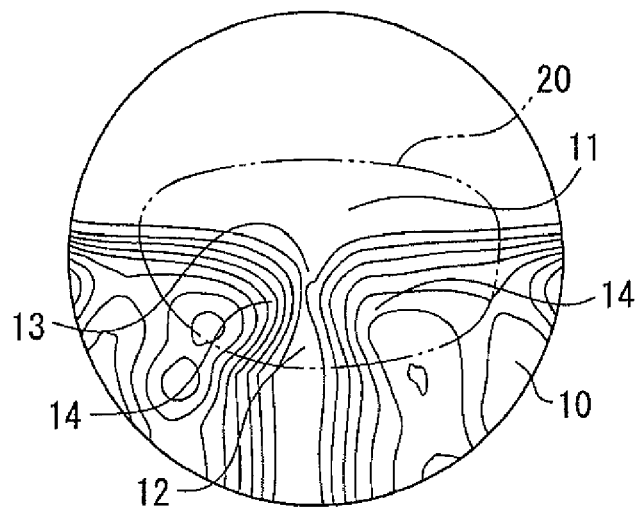
FIG. 12A is an aberration view of an A-type spectacle lens with a wide distance portion area.
Figure 12B:
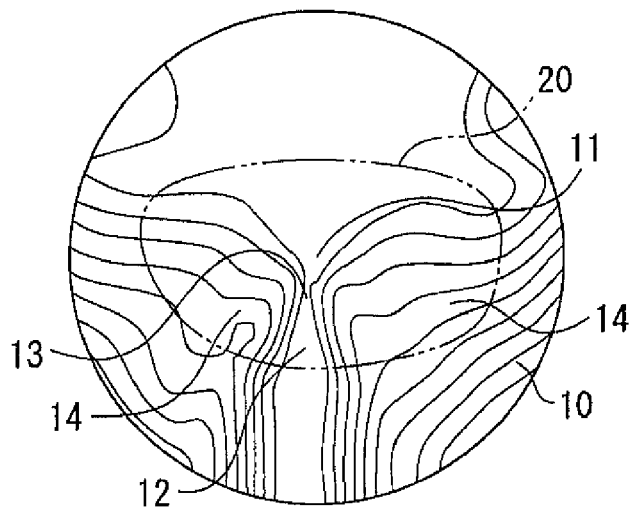
FIG. 12B is an aberration view of a B-type spectacle lens with an intermediate distance portion area.
Figure 12C:
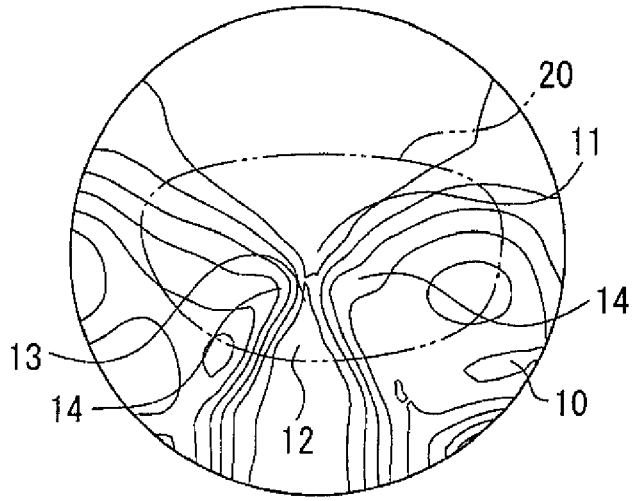
FIG. 12C is an aberration view of a C-type spectacle lens with a narrow distance portion area.

FIGS. 12A to 12C are aberration views of the A-type to C-type spectacle lenses 10. FIG. 12A shows the A-type spectacle lens 10; FIG. 12B shows the B-type spectacle lens; and FIG. 12C shows the C-type spectacle lens 10.

Since the A-type spectacle lens 10 with the wide distance portion area 11 shown in FIG. 12A has a large aberration in the side area 14, it is not suited to a wearer who uses a progressive power spectacle lens for the first time. However, since the C-type spectacle lens 10 with the narrow distance portion area 11 shown in FIG. 12C has a small aberration in the side area 14, it is suited to the wearer who uses a progressive power spectacle lens for the first time. The spectacle lens 10 with the intermediate distance portion area 11 shown in FIG. 12B is intermediate between the type A and the type C.

In FIG. 2, the judging part 704 judges, based on data from the computing part 702 and the lens type profile part 703, whether or not the conditions of 0 mm$\leq \Delta E \leq$2 mm, and 0 mm$<\Delta$Bh are satisfied when 4 mm$\leq$Fh, 3 mm$<$Fh$<$4 mm, and 1 mm$\leq$Fh$\leq$3 mm, for each of the far- and near-focused spectacle lens 10, the intermediate- and near-focused spectacle lens 10, and the near- and near-focused spectacle lens 10.

The specific configuration of the judging part 704 will be described based on FIG. 13.

Figure 13:
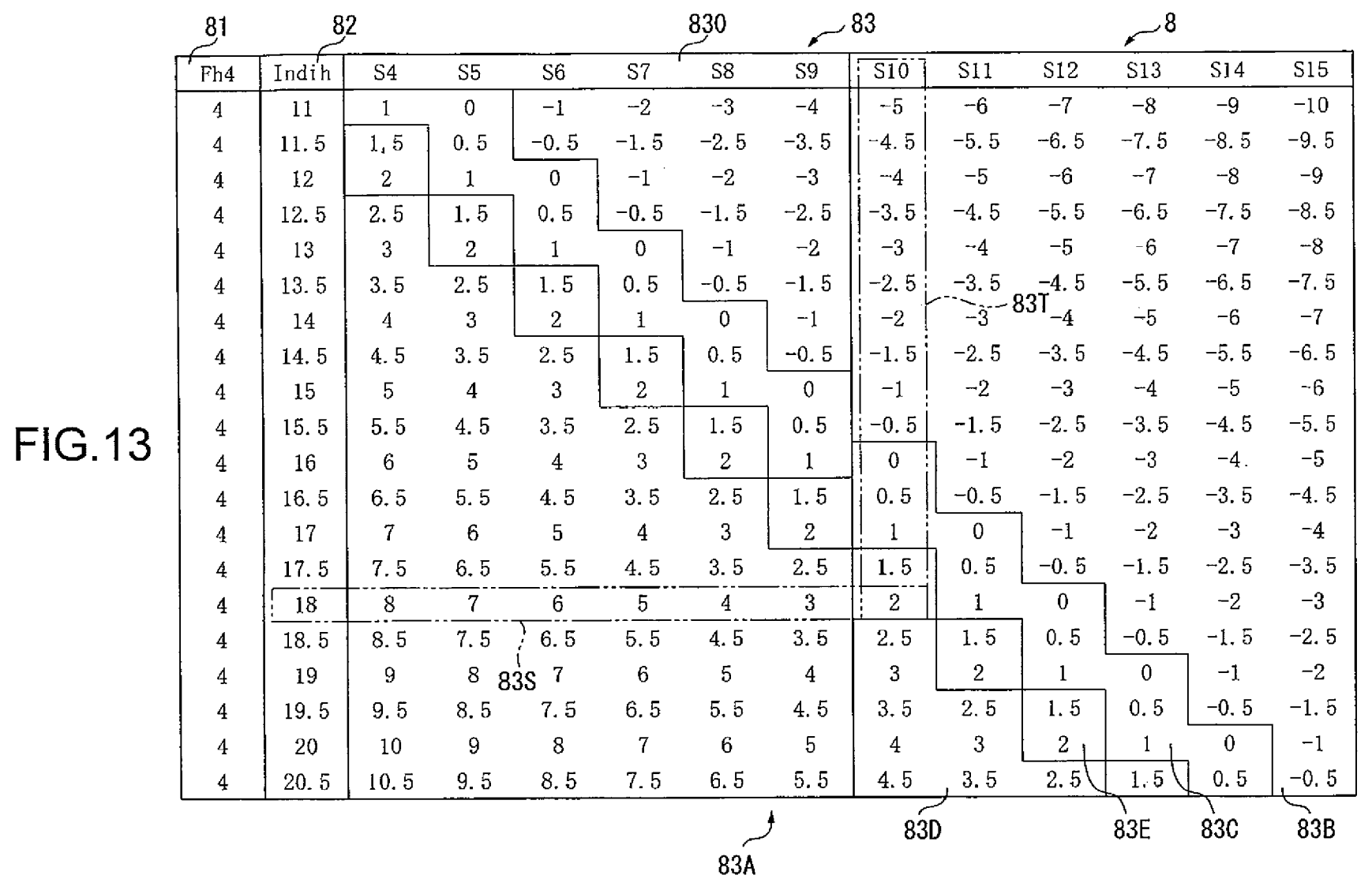

FIG. 13 shows a table 8 showing the results computed in the computing part 702.

In FIG. 13, an Fh setting column 81 for setting the distance-vision eye point height Fh is shown in the leftmost column, and an eyeball downward rotation amount display column 82 for displaying the downward rotation amount Indih of eyeball is shown to the right of the Fh setting column 81. In the eyeball downward rotation amount display column 82, the downward rotation amount Indih of eyeball is displayed in units of 0.5 mm. To the right of the eyeball downward rotation amount display column 82, a computation result display part 83 is shown. In the computation result display part 83, the computed value of $\Delta E$ based on the equation (h) is displayed corresponding to the numerical value of the downward rotation amount Indih of eyeball displayed in the eyeball downward rotation amount display column 82. In an uppermost row 830 of the computation result display part 83, the standard length of the progressive zone length is displayed.

The judging part 704 divides the computed values into a usable area 83A where $\Delta E$ is 0 mm or more and an unusable area 83B where $\Delta E$ takes negative numerical values. Further, the usable area 83A is divided into a border area 83C where $\Delta E$ takes numerical values of 0 mm$\leq \Delta E \leq$1 mm and a safety area 83D where $\Delta E$ takes numerical values of 1 mm$<\Delta E$. In the safety area 83D, the smaller numerical values of $\Delta E$ are preferred. In the embodiment, a range where $\Delta E$ takes numerical values of 1 mm$<\Delta E \leq$2 mm is used as an optimum area 83E.

For example, if the downward rotation amount Indih of eyeball is 18 mm, the numerical values in a range shown in a row 83S of the safety area 83D are usable, and a standard progressive zone length S corresponding to the smallest numerical value "2" among the numerical values shown in the row 83S is 10 mm. In the column of S10, a numerical value included in the optimum area 83E is "2".

A small numerical value (value of the optimum area 83E) is selected from the corresponding plurality of values in the row 83S within the range of the safety area 83D because of the following reason.

Figure 14A:
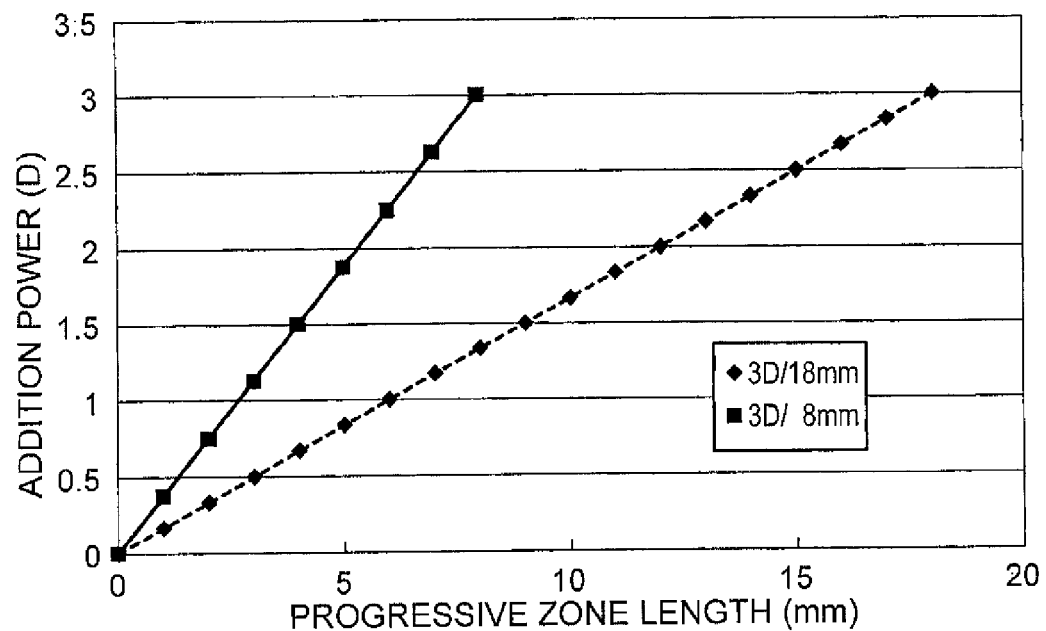
FIG. 14A is a graph of addition power characteristics of a progressive zone.
Figure 14B:
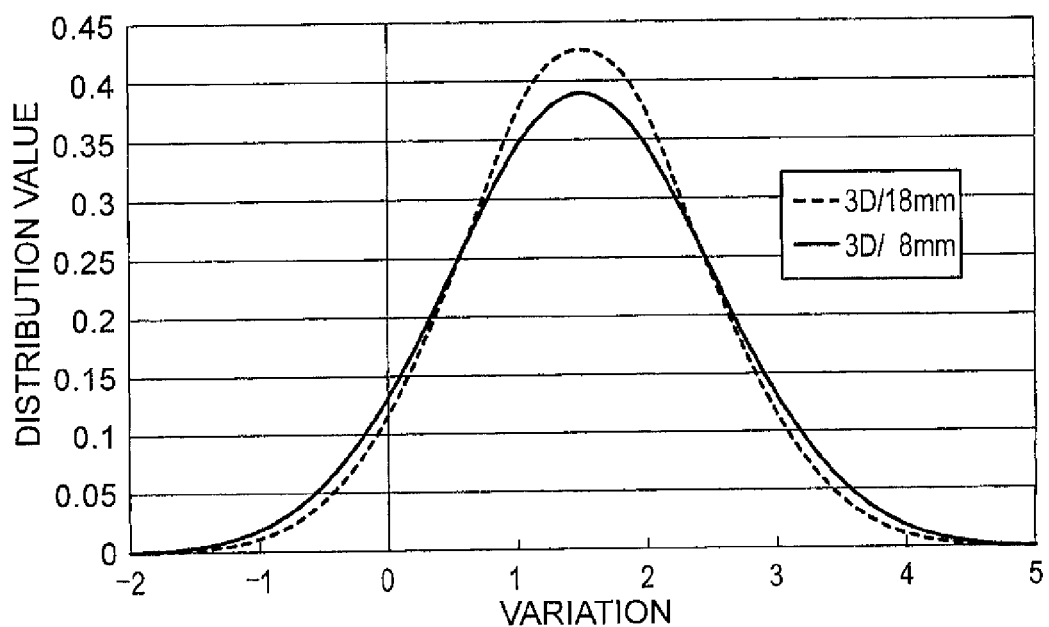
FIG. 14B is a graph of optical characteristics of the progressive zone.

FIG. 14A is a graph of addition power characteristics of the progressive zone; and FIG. 14B is a graph of optical characteristics of the progressive zone. FIG. 14A shows two examples in which the progressive zone length is set to 18 mm and 8 mm for increasing the addition power by 3D. From FIG. 14B, variation is smaller in the case of setting the progressive zone length to 18 mm than in the case of setting to 8 mm for increasing the addition power by 3D. That is, it is understood from FIGS. 14A and 14B that, for increasing the addition power by the same diopter, the greater progressive zone length causes less blurring and provides a good vision for the wearer. By the equations (h) and (i), as the progressive zone length SPh is greater, $\Delta E$ becomes smaller. Accordingly, a spectacle lens that causes less blurring and provides a good vision for the wearer is a spectacle lens having a small $\Delta E$. In the embodiment, when there are multiple choices for the progressive zone length, the smallest numerical value in the numerical values in the row 83S of the safety area 83D is selected.

In the example shown in FIG. 13, the judging part 704 uses the small numerical value of "2" included in the row 83S in the safety area 83D as $\Delta E$.

Returning to FIG. 2, frame data; wearing data; prescription data; the types of spectacle lenses using the size of the distance portion area 11 as a reference, i.e., the type A with the wide distance portion area 11, the type B with the intermediate distance portion area, and the type C with the narrow distance portion area 11; the types of spectacle lenses using the purpose of use as a reference, i.e., far and near focusing, intermediate and near focusing, near and near focusing; lens fabrication data; and other information necessary for manufacturing the lens are output from the spectacle information data input part 701 and the judging part 704 to the data output section 73. For example, specific examples of the data output section 73 include a display or the like.

Next, a method for selecting a spectacle lens according to the embodiment of the invention will be described.

Step of Determining Horizontal Field-of-Fixation Width

A step of determining the horizontal field-of-fixation width is a step of determining the horizontal field-of-fixation width Fw extending horizontally from the distance-vision eye point FP. The horizontal field-of-fixation width Fw is calculated based on the spectacle wearing distance EL and the horizontal field-of-fixation angle Fa that is previously set.

Step of Measuring Downward Rotation Amount of Eyeball

A step of measuring the downward rotation amount of eyeball is a step of determining the downward rotation amount Indih of eyeball using the apparatus 1 for measuring the downward rotation amount of eyeball.

Figure 15:
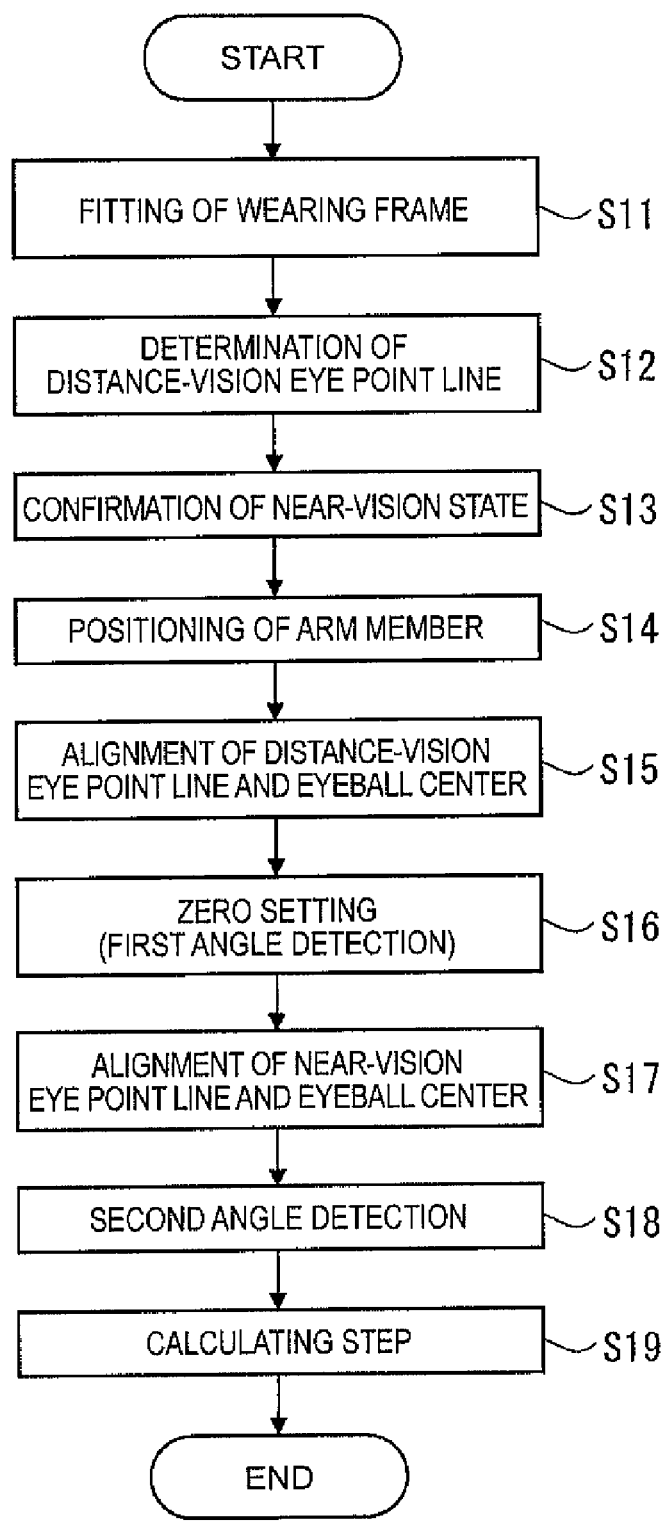
FIG. 15 is a flowchart showing one example of procedures for determining a downward rotation amount of eyeball.

These steps are implemented according to procedures shown in FIG. 15.

As shown in FIG. 3, a wearer first sits on the wearer chair 302 on one side, for example, on the left shown in the drawing between the two wearer chairs 302 of the apparatus 1 for measuring the downward rotation amount of eyeball, and fitting of a wearing frame is performed (S11). In this step, the wearer sat on the wearer chair 302 wears spectacles with the spectacle lenses 10 as test objects and is caused to direct his/her line of sight forward so as to look into the far distance in a natural state. In this step, the side image of the wearer is picked up by the side image pickup unit 4 to determine the spectacle wearing distance EL.

Thereafter, the distance-vision eye point line of one eye of the wearer, for example, the left eye is determined (S12). To this end, the wearer is caused to face forward; a position corresponding to a pupil portion EC of the wearer in the spectacle lens 10 is determined as the distance-vision eye point line; and an examiner marks this position on the spectacle lens on one side with a predetermined mark, for example, in red. Further, a near vision state is confirmed in a head position free environment (S13). The wearer is caused to set his/her head portion in a natural state, and the position of the near-vision eye point is estimated.

Thereafter, a step of positioning the arm member is implemented (S14). To this end, the arm supporting member 31 is rotated with respect to the supporting column 301; the arm supporting member 31 is expanded or contracted; the arm member 32 is rotated with respect to the arm supporting member 31 to position the rotation portion 312A as a rotatable end portion of the arm member 32 at the side surface of the eyeball E of the wearer (refer to FIG. 4).

Thereafter, the distance-vision eye point line and the pupil portion EC as an eyeball center of the wearer are aligned (S15). To this end, the wearer is caused to look at the portion marked as the distance-vision eye point line; and the front image of the wearer is picked up by the camera 33 (refer to FIG. 5A). The examiner confirms the image 33A picked up by the camera 33 while seeing it; the inclination angle of the arm member 32 at that time is set to zero by the arm rotation angle detecting unit 34; and the inclination angle set to zero is detected as a first angle (S16). The operation for the zero setting is also possible through the input unit such as a keyboard of the computing unit 5.

Next, the near-vision eye point line and the eyeball center of the wearer are aligned (S17). To this end, the wearer is caused to naturally lower his/her line of sight. As shown in FIG. 3 for example, the wearer holds a document D in his/her hand and naturally drops the line of sight toward the document D at hand. The arm member 32 is rotated until the pupil portion EC of the wearer is positioned on the near-vision eye point line at the front (refer to FIG. 5B). Along with the rotation of the arm member 32, the numerical value of the inclination angle displayed in the inclination angle display part 33B increases. When the pupil portion EC of the wearer is positioned on the near-vision eye point line at the front, the examiner confirms it while seeing the image 33A picked up by the camera 33, and the inclination angle of the arm member 32 at that time is detected as a second angle by the arm rotation angle detecting unit 34 (S18). The camera 33 is slowly moved downward until the position of the lower end 20P of the spectacle lens 10 comes to the front position; the position is determined; and the apparent length M between the near-vision eye point NP and the lower end 20P of the spectacle lens 10 is measured.

Further, based on the inclination angle detected in the second angle detecting step, a distance between the position of the distance-vision eye point FP and the position of the near-vision eye point NP is calculated by the computing unit 5 (S19).

Figure 16:
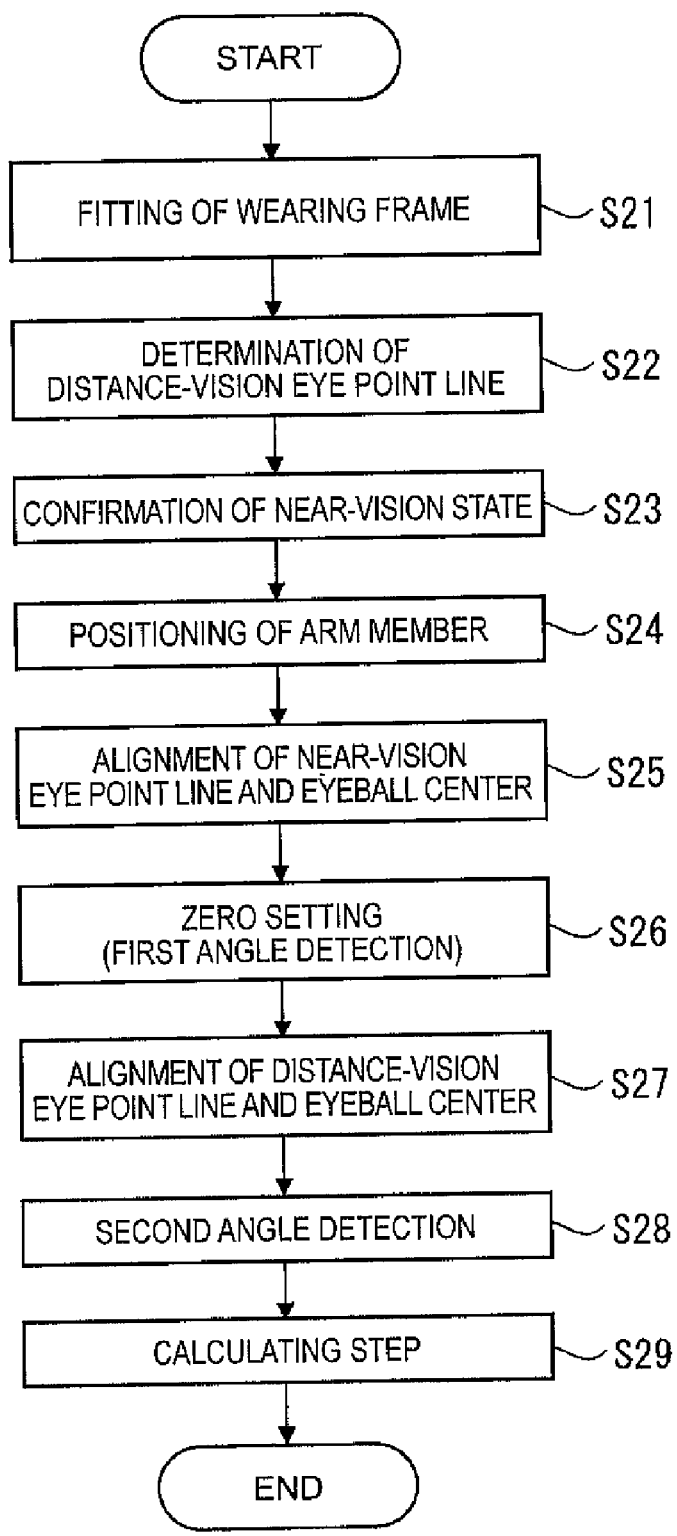
FIG. 16 is a flowchart showing another example of procedures for determining a downward rotation amount of eyeball.

In this case, the embodiment is not limited to the procedures shown in FIG. 15 but can be implemented by procedures shown in FIG. 16. That is, it is detected that the pupil of the wearer is positioned at the near-vision eye point at the front in the state where the wearer lowers the line of sight in the first angle detecting step (S25 and S26); it is detected that the pupil portion EC of the wearer is positioned on the distance-vision eye point line at the front in a state where the wearer raises the line of sight (S27); and the inclination angle of the arm member 32 at the front position is detected in the second angle detecting step (S28). The other procedures S21 to S24 and S29 are the same as the procedures S11 to S14 and S19 shown in FIG. 15.

In the computing unit 5, the downward rotation amount Indih of eyeball is calculated based on the above-described equations (a) to (f).

In the embodiment, the downward rotation amount Indih of eyeball is calculated for both eyes. To this end, for the other eye for which the calculation is not performed in the above-described steps, for example, for the right eye, the same steps are implemented. First, the wearer leaves the left wearer chair 302 on which the wearer has sat and sits anew on the right wearer chair 302, and the arm supporting member 31 is rotated by 180 degrees or more with respect to the supporting column 301. This enables the camera 33 to pick up a front image of the wearer focusing on the right eye. Then, the above-described steps are implemented also for the right eye.

The method for selecting the spectacle lens will be described according to a flowchart of FIG. 17.

Figure 17:
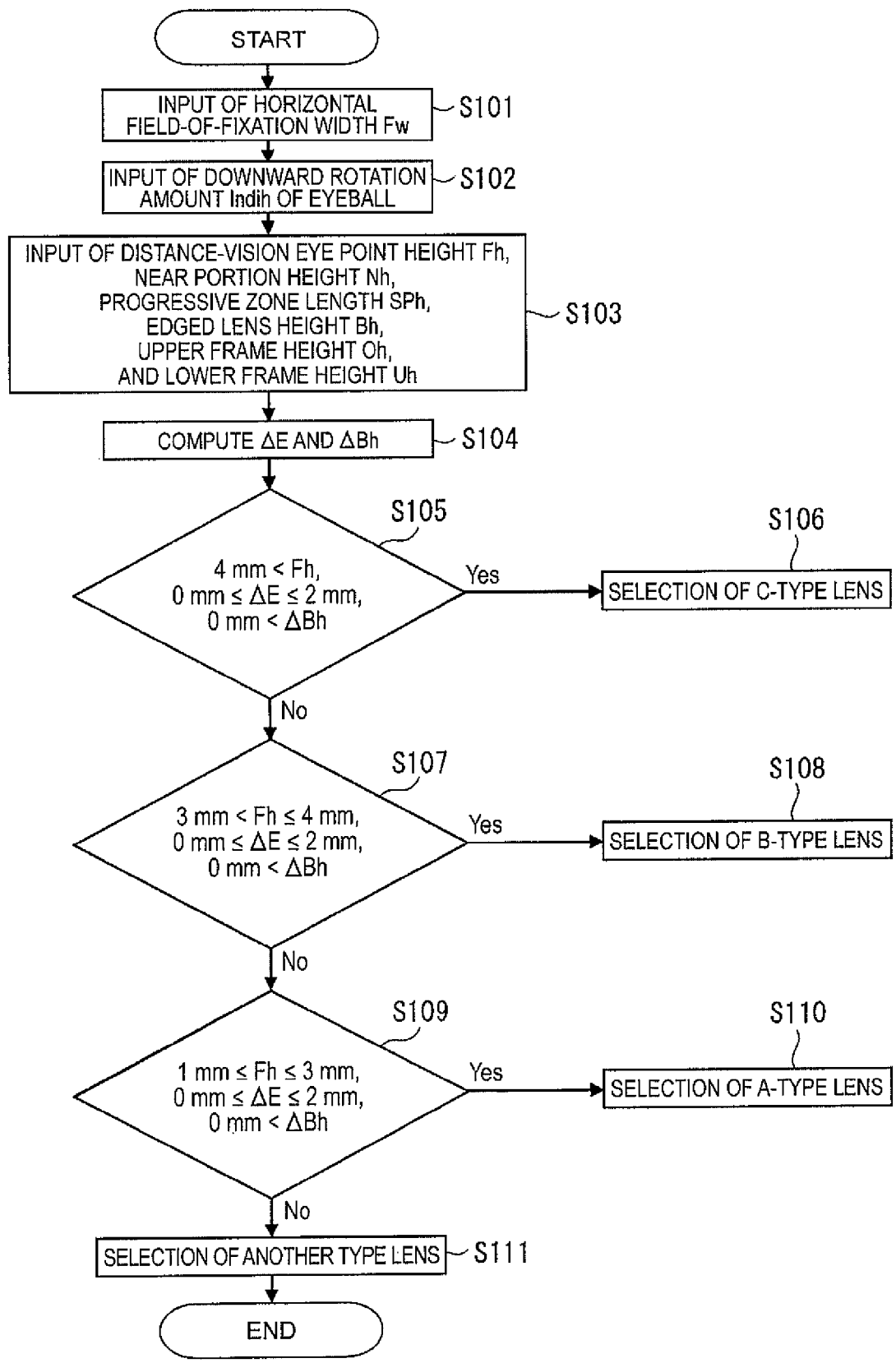
FIG. 17 is a flowchart for explaining a method for selecting a spectacle lens.

As shown in FIG. 17, data of the horizontal field-of-fixation width Fw is first input to the selection apparatus 7 (S101). Further, data of the downward rotation amount Indih of eyeball is input to the selection apparatus 7 (S102).

Then, the distance-vision eye point height Fh, the near portion height Nh, the edged lens height Bh, the progressive zone length SPh, the upper frame height Oh, the lower frame height Uh, other lens information, and frame information are input to the selection apparatus 7 (S103).

Step of Computing

The above pieces of data are sent to the computing part 702. In the computing part 702, $\Delta E$ is computed based on the downward rotation amount Indih of eyeball, the distance-vision eye point height Fh, the progressive zone length SPh, and the near portion height Nh. Further, $\Delta Bh$ is computed based on the $\Delta E$, the edged lens height Bh, the upper frame height Oh, the distance-vision eye point height Fh, the progressive zone length SPh, the near portion height Nh, and the lower frame height Uh (S104).

Step of Judging

Based on the computed result from the computing part 702 and the horizontal field-of-fixation width Fw, the judging part 704 makes a judgment for each of the three kinds of the spectacle lenses 10 as described above.

Figure 18A:
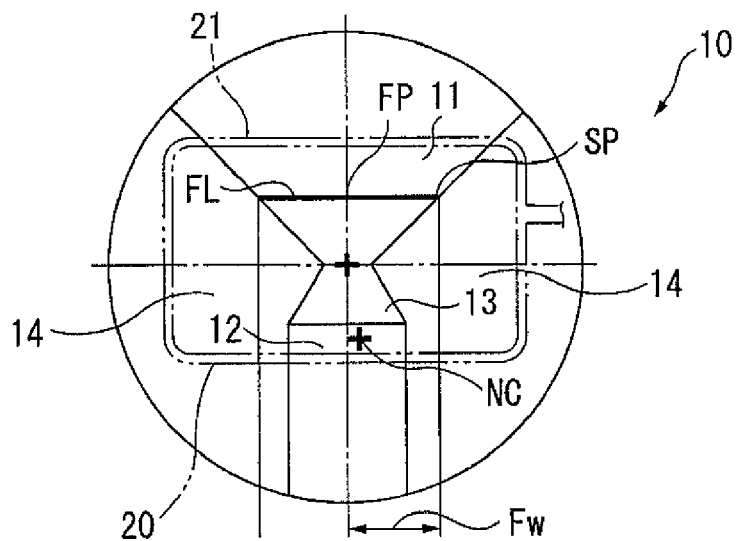
FIGS. 18A to 18C are schematic views showing three types of spectacle lenses different in size of the distance portion area in far- and near-focused type spectacle lenses.
Figure 18B:
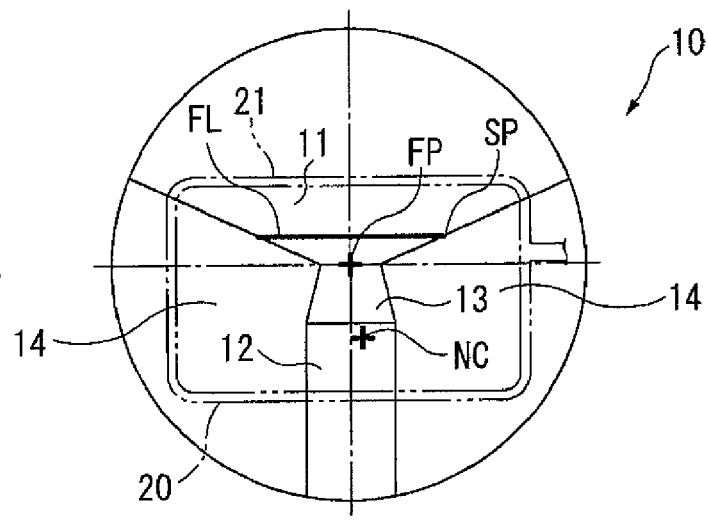
Figure 18C:
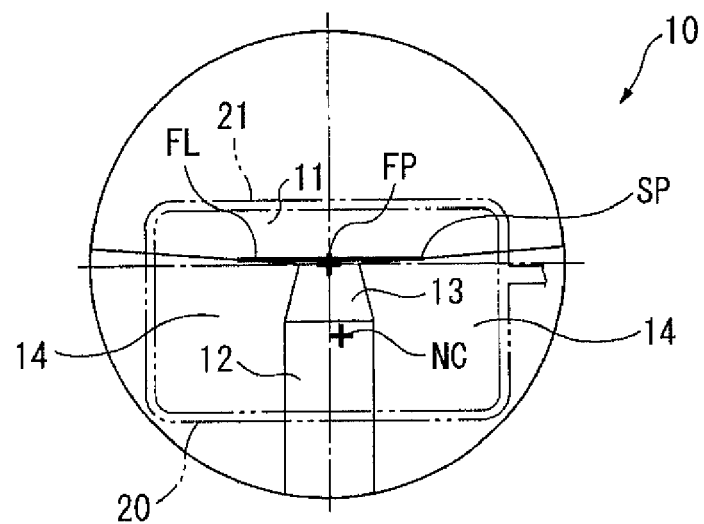

In the far- and near-focused type spectacle lenses 10 shown in FIGS. 18A to 18C for example, it is judged whether or not the conditions of Fh>4 mm, 0 mm$\leq\Delta E\leq$2 mm, and 0 mm<$\Delta Bh$ are satisfied (S105). If the conditions are satisfied, the C-type spectacle lens 10 shown in FIG. 18A is selected (S106). If the conditions are not satisfied, it is judged whether or not the B-type lens satisfies the conditions (S107).

The selecting conditions for the B-type lens are 3 mm<Fh$\leq$4 mm, 0 mm$\leq\Delta E\leq$2 mm, and 0 mm<$\Delta Bh$. If these conditions are satisfied, the B-type spectacle lens 10 shown in FIG. 18B is selected (S108). If the conditions are not satisfied, it is judged whether or not the A-type lens satisfies the conditions (S109).

The selecting conditions for the A-type lens are 1 mm$\leq$Fh$\leq$3 mm, 0 mm$\leq\Delta E\leq$2 mm, and 0 mm<$\Delta Bh$. If these conditions are satisfied, the A-type spectacle lens 10 shown in FIG. 18C is selected (S110). If the conditions are not satisfied, another lens other than the A- to C-type lenses is selected (S111).

Figure 19A:
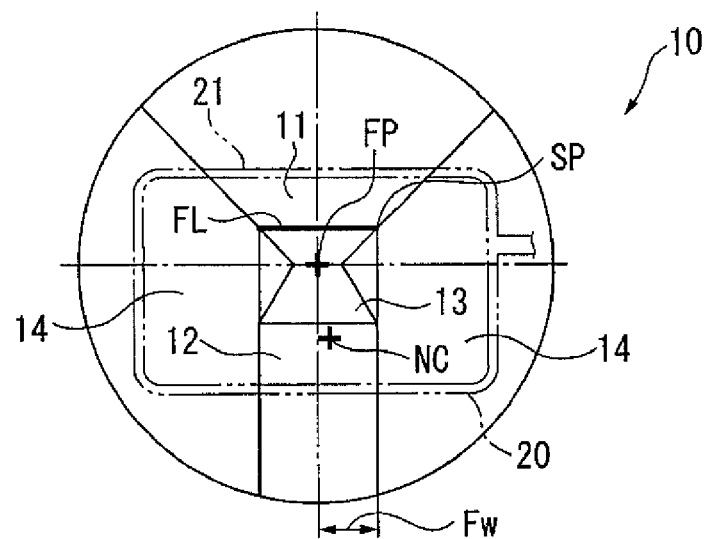
FIGS. 19A to 19C are schematic views showing three types of spectacle lenses different in size of the distance portion area in intermediate- and near-focused type spectacle lenses.
Figure 19B:
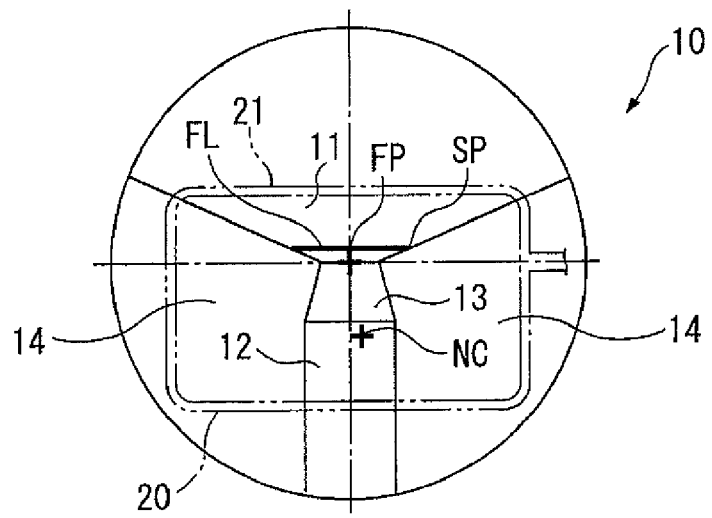
Figure 19C:
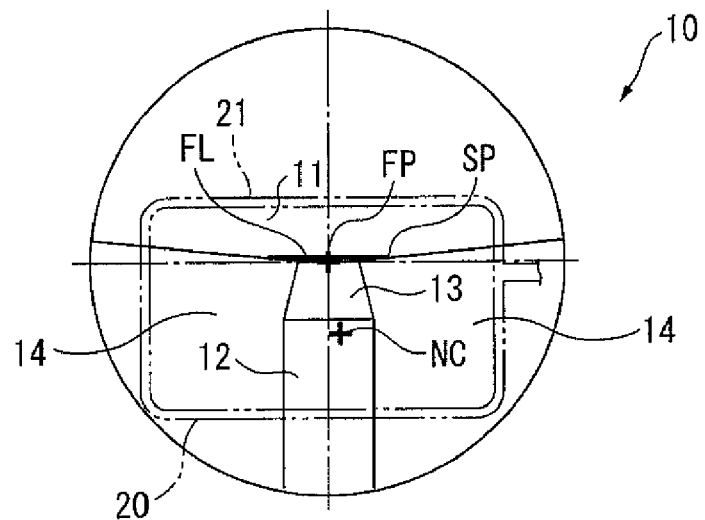

In the intermediate- and near-focused type spectacle lenses 10 shown in FIGS. 19A to 19C, according to the flowchart shown in FIG. 17, the selection of the C-type spectacle lens 10 shown in FIG. 19A is implemented; the selection of the B-type spectacle lens 10 shown in FIG. 19B is implemented; and the selection of the A-type spectacle lens 10 shown in FIG. 19C or another lens is implemented.

Figure 20A:
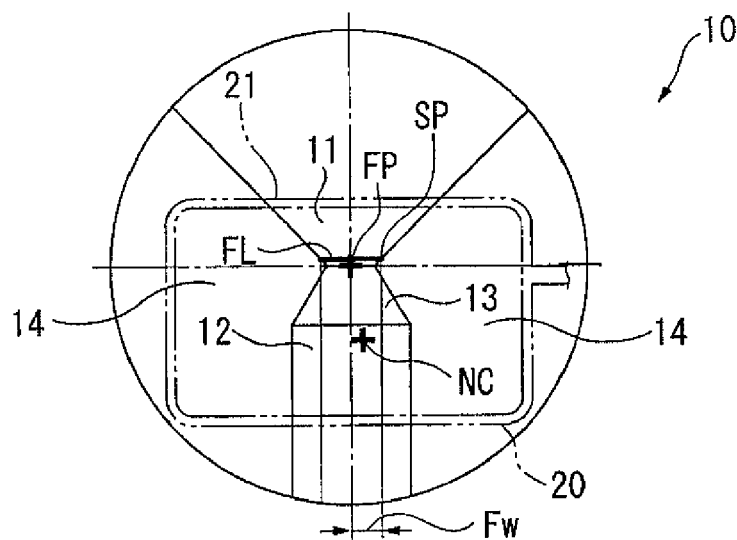
FIGS. 20A to 20C are schematic views showing three types of spectacle lenses different in size of the distance portion area in near- and near-focused type spectacle lenses.
Figure 20B:
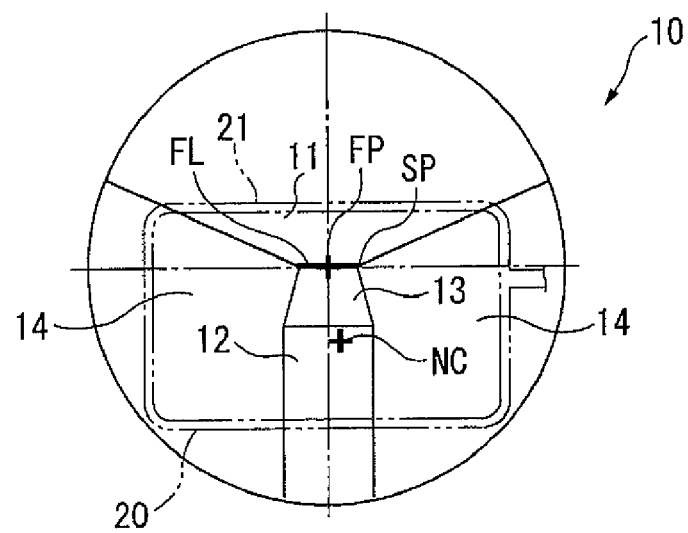
Figure 20C:
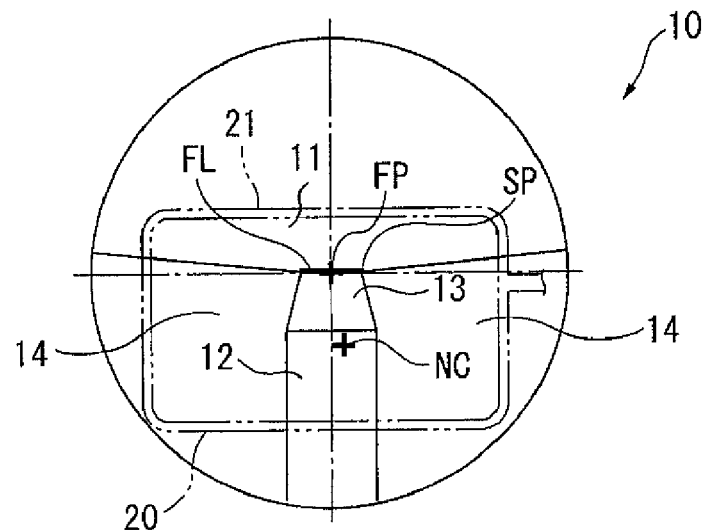

In the near- and near-focused type spectacle lenses 10 shown in FIGS. 20A to 20C, according to the flowchart shown in FIG. 17, the selection of the C-type spectacle lens 10 shown in FIG. 20A is implemented; the selection of the B-type spectacle lens 10 shown in FIG. 20B is implemented; and the selection of the A-type spectacle lens 10 shown in FIG. 20C or another lens is implemented.

However, the intermediate- and near-focused spectacle lens 10 and the near- and near-focused spectacle lens 10 are different in the horizontal field-of-fixation width Fw from the far- and near-focused spectacle lens 10 shown in FIGS. 18A to 18C.

In the embodiment, the selection of the spectacle lens 10 described in the above steps is implemented for the right and left eyes.

Accordingly, the following operation and effect can be provided in the embodiment.

(1) The apparatus 1 for measuring the downward rotation amount of eyeball is configured to include the line-of-sight position detecting unit 3 that detects the position of the front line of sight LF corresponding to the distance-vision eye point FP of a wearer and the position of the downward line of sight LN corresponding to the near-vision eye point NP, and the computing unit 5 that computes the distance between the position of the distance-vision eye point FP and the position of the near-vision eye point NP detected by the line-of-sight position detecting unit 3. When the downward rotation amount Indih of eyeball is measured, since the wearer is in a state of wearing spectacles, the distance-vision eye point FP and the near-vision eye point NP can be accurately detected regardless of the wearer's posture. Therefore, the downward rotation amount Indih of eyeball can be measured accurately and simply at low cost.

(2) The line-of-sight position detecting unit 3 is configured to include the arm member 32 that is rotatable at its base end and positioned at the lateral position of the eyeball E of the wearer, the camera 33 that is disposed on the distal end side of the arm member 32 and detects the front position of the eyeball E of the wearer, and the arm rotation angle detecting unit 34 that detects the rotation angle of the arm member 32. Therefore, the distance-vision eye point FP and the near-vision eye point NP can be detected in a natural posture regardless of the wearer's posture, and the downward rotation amount Indih of eyeball can be measured accurately and simply. Especially when the distance-vision eye point FP and the near-vision eye point NP are determined, the position of the pupil portion EC of the wearer is not detected based on an image but is determined based on the inclination angle of the arm member 32. Therefore, the structure of the line-of-sight position detecting unit 3 is more simplified, and the cost reduction in the apparatus can be ensured. In the embodiment, it is necessary to set the base end of the arm member 32 at the lateral side of the eyeball E of the wearer. However, as shown in a graph of FIG. 21 showing the relation between the setting error of the arm member and the error of the downward rotation amount of eyeball, even when the setting error is in a range of from +5.0 mm to −5.0 mm, the final error of the downward rotation amount of eyeball falls within a range of from +0.30 mm to −0.3 mm, in samples indicated as S1 to S10. It can be seen that the influence caused by the setting error is, in effect, small.

(3) The base end side of the arm member 32 is rotatably supported to the arm supporting member 31, and the arm supporting member 31 is rotatably attached to the supporting column 301. Therefore, by adjusting the rotation angle of the arm member 32 with respect to the arm supporting member 31 and adjusting the rotation angle of the arm supporting member 31 with respect to the supporting column 301, the positioning of the rotatable base end of the arm member 32 at the lateral position of the eyeball E of the wearer can be performed easily. Therefore, the measurement of the downward rotation amount Indih of eyeball can be performed accurately.

(4) The arm supporting member 31 is configured to include the rectangular column portion 310 whose base end portion is freely rotatably supported to the supporting column 301 and the rectangular tube portion 311 in which the rectangular column portion 310 is freely telescopically housed, and is freely telescopically configured in its axial direction. Therefore, by expanding or contracting the arm supporting member 31, the positioning of the rotatable base end of the arm member 32 to the wearer can be performed more easily.

(5) The wearer chairs 302 are each arranged on opposite sides of the supporting column 301, and the distal end side of the arm supporting member 31 is made rotatable so as to be positioned on the opposite sides of the supporting column 301 corresponding to the wearer chairs 302. Therefore, even when the downward rotation amount Indih of eyeball is different between the right and left eyeballs of the wearer, the different downward rotation amounts Indih of the right and left eyeballs can be accurately measured.

(6) Since the camera 33 is used for picking up a front image of the wearer, the front position of the wearer can be picked up accurately and reliably. That is, by effectively utilizing the focusing function of the camera 33 according to the size of the wearer's face, an image of the wearer can be picked up with good accuracy, and further the cost of the apparatus itself can be reduced.

(7) The computing unit 5 is configured to compute the length N of the near-vision eye point by the above-described equations (a) to (d) based on the forward tilt angle $\theta$, the angle $\beta$ between the downward line of sight LN and the eyeball-side flat surface OL of the spectacle lens 10, the angle $\gamma$ between the eyeball-side flat surface OL of the spectacle lens 10 and the front line of sight LF, the angle $\delta$ between the eyeball-side flat surface OL of the spectacle lens 10 and the normal line VL drawn from the position of the lower end 20P of the frame 20 on the spectacle side surface to the downward line of sight LN, and the distance M of the normal line VL drawing from the position of the lower end 20P to the downward line of sight LN. Therefore, by previously registering the equations (a) to (d) in the memory of the computing unit 5, the length N of the near-vision eye point can be calculated simply and accurately regardless of the thickness of the spectacle lens 10.

(8) The computing unit 5 is configured to compute the length L of the distance-vision eye point by the above-described equation (e) based on the forward tilt angle $\theta$ and the distance K between the position of the lower end 20P of the frame and the front line of sight LF. Therefore, by previously registering the equation (e) in the memory of the computing unit 5, the length L of the distance-vision eye point can be calculated simply and accurately regardless of the thickness of the spectacle lens 10.

(9) Since the side image pickup unit 4 that measures the forward tilt angle $\theta$ of the frame 20 is provided, the forward tilt angle $\theta$ can be measured in a state where the wearer wears spectacles. Therefore, the forward tilt angle $\theta$ can be determined accurately regardless of the wearing state.

(10) The wearer is caused to face forward in the state of wearing the spectacle lens 10 and a position corresponding to the pupil portion EC is determined as the distance-vision eye point line; the rotatable base end of the arm member 32 is positioned at the lateral position of the eyeball E of the wearer; it is detected by the camera 33 that the pupil portion EC of the wearer is positioned on the distance-vision eye point line at the front, and the inclination angle of the arm member 32 at the front position is detected by the arm rotation angle detecting unit 34; it is detected by the camera 33 that the pupil portion EC is positioned at the near-vision eye point at the front in the state where the wearer lowers the line of sight, and the inclination angle of the arm member 32 at this position is detected by the arm rotation angle detecting unit 34; and based on the downward rotation angle $\alpha$ of eyeball determined from the difference between the inclination angles detected in these steps, the distance between the position of the distance-vision eye point FP and the position of the near-vision eye point NP is determined. With this configuration, the downward rotation amount Indih of eyeball can be determined simply using the apparatus having the above-described configuration.

(11) Similarly, the wearer is caused to face forward in the state of wearing the spectacle lens 10 and a position corresponding to the pupil portion EC is determined as the distance-vision eye point line; the rotatable base end of the arm member 32 is positioned at the lateral position of the eyeball E of the wearer; it is detected by the camera 33 that the pupil, portion EC of the wearer is positioned on the near-vision eye point line at the front, and the inclination angle of the arm member 32 at the front position is detected by the arm rotation angle detecting unit 34; it is detected by the camera 33 that the pupil portion EC is positioned at the distance-vision eye point at the front in the state where the wearer raises the line of sight, and the inclination angle of the arm member 32 at this position is detected by the arm rotation angle detecting unit 34; and based on the downward rotation angle α of eyeball determined from the difference between the inclination angles detected in these steps, the distance between the position of the distance-vision eye point FP and the position of the near-vision eye point NL is determined. With this configuration, the downward rotation amount Indih of eyeball can be determined simply using the apparatus having the above-described configuration.

The invention is not limited to the above-described embodiment. It is needless to say that modifications and improvements within a range in which advantages and effects of the invention can be attained are included in the contents of the invention.

In the embodiment for example, the downward rotation amount Indih of eyeball is calculated for both eyes to select the spectacle lens 10. In the invention, however, the downward rotation amount Indih of eyeball may be calculated only for an eye on one side, for example, a left eye to select the spectacle lens 10. For example, the hole-in-card test may be used to determine a dominant eye, and the downward rotation amount Indih of eyeball is calculated only for the dominant eye to select the spectacle lens 10.

In the embodiment, the arm rotation angle detecting unit 34 is configured to be able to be set to zero. In the invention, however, the arm rotation angle detecting unit 34 may not be configured to be able to be set to zero, and information of the inclination angle of the arm member 32 with respect to a horizontal plane may be directly output to the computing unit 5 to determine the difference between the inclination angles by the computing unit 5.

In the embodiment, a most suitable spectacle lens 10 is selected from the three types of the spectacle lenses 10, i.e., the type A with the wide distance portion area 11, the type B with the intermediate distance portion area 11, and the type C with the narrow distance portion area 11. In the invention, however, the size of the distance portion area 11 may be roughly classified into two sizes, so that one spectacle lens may be selected from these two types. Or, the size of the distance portion area 11 may be classified into four or more sizes, so that one spectacle lens may be selected from these four or more types.

Further, in the step of determining the horizontal field-of-fixation width, the horizontal field-of-fixation angle Fa may be set according to an individual wearer. Moreover, the horizontal field-of-fixation angle Fa may be used in common among the far- and near-focused spectacle lens 10, the intermediate- and near-focused spectacle lens 10, and the near- and near-focused spectacle lens 10.

Moreover, the table 8 shown in FIG. 13 may be previously prepared as a manual to select the spectacle lens based on the manual.

In the embodiment, the apparatus 1 for measuring the downward rotation amount of eyeball is configured to include the side image pickup unit 4 that measures the forward tilt angle θ of the frame 20. In the invention, however, the design data of the forward tilt angle θ can be used as it is for the measurement of the downward rotation amount of eyeball as long as the wearer wears spectacles in a correct posture, so that the side image pickup unit 4 can be omitted.

The image 33A does not necessarily include the inclination angle display part 33B.

The invention can be widely utilized in a spectacle store or the like as an apparatus for selecting a progressive power lens.

The entire disclosure of Japanese Patent Application No: 2009-229408, filed Oct. 1, 2009 is expressly incorporated by reference herein.

What is claimed is:

1. An apparatus for measuring a downward rotation amount of eyeball that measures a length from a distance-vision eye point to a near-vision eye point of a spectacle lens actually worn by a wearer and attached to a frame having an upper side portion and a lower side portion, comprising:
a line-of-sight position detecting unit that detects a position of a line of sight corresponding to the distance-vision eye point of the wearer and a position of a line of sight corresponding to the near-vision eye point; and
a computing unit that computes a distance between the position of the distance-vision eye point and the position of the near-vision eye point detected by the line-of-sight position detecting unit, wherein
the line-of-sight position detecting unit has an arm member that is rotatable at one end and positioned at a lateral position of an eyeball of the wearer, a front detecting mechanism that is disposed on the other end side of the arm member and detects a front position of the eyeball of the wearer, and an arm rotation angle detecting unit that detects a rotation angle of the arm member.

2. The apparatus for measuring the downward rotation amount of eyeball according to claim 1, wherein
the arm member is rotatably supported to an arm supporting member at the one end side, and the arm supporting member is rotatably attached to a supporting column.

3. The apparatus for measuring the downward rotation amount of eyeball according to claim 2, wherein
the arm supporting member can expand and contract.

4. The apparatus for measuring the downward rotation amount of eyeball according to claim 3, further comprising wearer chairs each arranged on opposite sides of the supporting column, wherein
the arm supporting member is rotatable at its distal end side so as to be positioned on opposite sides of the supporting column.

5. The apparatus for measuring the downward rotation amount of eyeball according to claim 1, wherein
the front detecting mechanism is a camera.

6. A method for measuring a downward rotation amount of eyeball using the apparatus for measuring the downward rotation amount of eyeball according to claim 1, comprising:
causing the wearer to face forward in a state of wearing the spectacle lens and determining a position of the spectacle lens corresponding to the pupil of the wearer as a distance-vision eye point line;
positioning the rotatable one end of the arm member at the lateral position of the eyeball of the wearer;
detecting, by the front detecting mechanism, that the pupil of the wearer is positioned on the distance-vision eye point line at the front and detecting, by the arm rotation angle detecting unit, an inclination angle of the arm member at this front position as a first angle;

detecting, by the front detecting mechanism, that the pupil of the wearer is positioned at the near-vision eye point at the front in a state where the wearer lowers his/her line of sight and detecting, by the arm rotation angle detecting unit, an inclination angle of the arm member at this position as a second angle; and calculating, by the computing unit, a distance between the position of the distance-vision eye point and the position of the near-vision eye point based on a downward rotation angle of eyeball determined from a difference between the inclination angle detected in the detecting the first angle and the inclination angle detected in the detecting the second angle.

7. A method for measuring a downward rotation amount of eyeball using the apparatus for measuring the downward rotation amount of eyeball according to claim 1, comprising:

causing the wearer to face forward in a state of wearing the spectacle lens and determining a position of the spectacle lens corresponding to the pupil of the wearer as a distance-vision eye point line;

positioning the rotatable one end of the arm member at the lateral position of the eyeball of the wearer;

detecting, by the front detecting mechanism, that the pupil of the wearer is positioned at the near-vision eye point at the front in a state where the wearer lowers his/her line of sight and detecting, by the arm rotation angle detecting unit, an inclination angle of the arm member at this position as a first angle;

detecting, by the front detecting mechanism, that the pupil of the wearer is positioned on the distance-vision eye point line at the front in a state where the wearer raises his/her line of sight and detecting, by the arm rotation angle detecting unit, an inclination angle of the arm member at this front position as a second angle; and calculating, by the computing unit, a distance between the position of the distance-vision eye point and the position of the near-vision eye point based on a downward rotation angle of eyeball determined from a difference between the inclination angle detected in the detecting the first angle and the inclination angle detected in the detecting the second angle.

* * * * *